United States Patent
Fujii et al.

(10) Patent No.: US 9,227,012 B2
(45) Date of Patent: Jan. 5, 2016

(54) WINGED MEDICAL NEEDLE DEVICE

(75) Inventors: Ryoji Fujii, Hiroshima (JP); Kenji Sawa, Hiroshima (JP); Raita Uematsu, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 1271 days.

(21) Appl. No.: 12/087,946

(22) PCT Filed: Jan. 19, 2007

(86) PCT No.: PCT/JP2007/050841
§ 371 (c)(1),
(2), (4) Date: Jul. 17, 2008

(87) PCT Pub. No.: WO2007/083770
PCT Pub. Date: Jul. 26, 2007

(65) Prior Publication Data
US 2009/0018511 A1    Jan. 15, 2009

(30) Foreign Application Priority Data

Jan. 20, 2006  (JP) .................. 2006-012117

(51) Int. Cl.
*A61M 5/158* (2006.01)
*A61M 25/06* (2006.01)
*A61M 5/32* (2006.01)

(52) U.S. Cl.
CPC .......... *A61M 5/158* (2013.01); *A61M 25/0631* (2013.01); *A61M 25/0637* (2013.01); *A61M 5/3243* (2013.01); *A61M 2005/3247* (2013.01)

(58) Field of Classification Search
CPC ............ A61M 5/158; A61M 25/0631; A61M 25/0637; A61M 5/3243; A61M 2005/3247
USPC .......... 604/110, 164.01, 164.08, 164.12, 171, 604/177, 192, 197, 198
See application file for complete search history.

(56) References Cited

U.S. PATENT DOCUMENTS 4,362,156 A    12/1982   Feller, Jr. et al.
4,834,718 A    5/1989    McDonald
(Continued)

FOREIGN PATENT DOCUMENTS

EP    1374934    1/2004
EP    1621221    2/2006
(Continued)

OTHER PUBLICATIONS

"Independent". Merriam-Webster Online Dictionary. <http://www.merriam-webster.com/dictionary/independent>.*
(Continued)

*Primary Examiner* — Emily Schmidt
*Assistant Examiner* — Lauren M Peng
(74) *Attorney, Agent, or Firm* — Hamre, Schumann, Mueller & Larson, P.C.

(57) ABSTRACT

The medical needle device includes: a shield 4 including a substantially cylindrical portion 4*a*; a tube 13; a first hub 2 that is inserted into an inner bore of the shield movably in an axial direction. The rear end of the first hub 2 is connected with the tube 3. A rigid needle 1 is fixed to a front end portion of the first hub; and a hub movement controlling member 14 that is attached to the shield detachably. The hub movement controlling member 14 includes: a stopper portion 14*a* that can be inserted from the rear end side of the shield into an inner bore of the shield exsertably.

28 Claims, 22 Drawing Sheets

(56) References Cited

U.S. PATENT DOCUMENTS

| | | | |
|---|---|---|---|
| 4,944,725 A | | 7/1990 | McDonald |
| 5,219,339 A | * | 6/1993 | Saito ............................. 604/198 |
| 5,545,146 A | | 8/1996 | Ishak |
| 5,738,660 A | | 4/1998 | Luther |
| 5,893,844 A | | 4/1999 | Misawa |
| 5,928,199 A | * | 7/1999 | Nakagami .................... 604/171 |
| 6,132,401 A | * | 10/2000 | Van Der Meyden et al. . 604/195 |
| 6,475,191 B2 | * | 11/2002 | Tamura et al. ............ 604/164.08 |
| 7,413,560 B2 | * | 8/2008 | Chong et al. ................... 604/174 |
| 2002/0169420 A1 | * | 11/2002 | Galt et al. ................. 604/164.12 |
| 2004/0225261 A1 | * | 11/2004 | Millerd ........................ 604/177 |
| 2004/0236287 A1 | | 11/2004 | Swenson et al. |
| 2005/0165355 A1 | * | 7/2005 | Fitzgerald ................ 604/164.08 |
| 2006/0079847 A1 | * | 4/2006 | Crawford ..................... 604/192 |
| 2010/0010453 A1 | * | 1/2010 | Riemelmoser ............... 604/198 |

FOREIGN PATENT DOCUMENTS

| | | |
|---|---|---|
| JP | 5-503019 | 5/1993 |
| JP | 10-501996 | 2/1998 |
| JP | 10-85333 | 4/1998 |
| JP | 10-258123 | 9/1998 |
| JP | 2003-116996 | 4/2003 |
| JP | 2003-175112 | 6/2003 |
| WO | 91/04761 | 4/1991 |

OTHER PUBLICATIONS

Extended European Search Report, Jan. 15, 2015; European Application No. 07707129.8 (7 pages).

Written Opinion; PCT/JP2007/050841 (3 pages).

* cited by examiner

WINGED MEDICAL NEEDLE DEVICE

TECHNICAL FIELD

The present invention relates to a medical needle device having a shield for preventing needle-stick injuries, in which a rigid needle can be stored safely after use.

BACKGROUND ART

Conventionally, contamination and infection due to needle-stick injuries from injection needles, puncture needles and the like have been a problem in medical facilities. In particular, recently, as hepatitis B, hepatitis C, HIV (human immunodeficiency virus) and the like have become a widespread social issue, there is a demand for systems that actively prevent the occurrence of accidents such as needle-stick injuries and the like.

As a way to prevent needle-stick injuries, various injection needle devices that have a structure in which a cannula is covered by a cover when injection needles or puncture needles are collected after use have been proposed. In most cases, such systems for preventing needle-stick injuries that have been proposed so far have cylindrical protection covers (hereinafter, referred to as shields), and the shields can slide with respect to rigid needles. That is, the system is configured such that the rigid needle either can be exposed or covered by the shield according to the sliding state of the shield.

Patent Document 1 discloses one example of a conventional medical needle device. This medical needle device includes: a winged shield 212 in which a wing portion 273 is connected with a substantially cylindrical shield tube (see FIG. 16); a hub 210 that is inserted into the shield tube movably in an axial direction and has a connection end 264 connected with an infusion tube (see FIG. 17); and a rigid needle that is fixed to the hub 210 (not illustrated). In the case where the hub 210 is positioned in an inner bore of the winged shield 212, the rigid needle protrudes toward an outside of the shield tube 212. The protruding rigid needle is stored into the inner bore of the winged shield 212 by allowing the hub 210 to slide toward a rear end side of the winged shield 212.

As shown in FIG. 18, in this conventional medical needle device, a contact surface 259 of the hub 210 (see FIG. 17) is in contact with an end surface on a rear end side of the winged shield 212, thereby preventing the hub 210 from slipping out from a front end side of the winged shield 212. At the same time, a protruding portion 234 that is positioned in a groove 236 functions to prevent the hub 210 from sliding toward a rear side. After puncturing in this state, the rigid needle is drawn into the winged shield 212, and a shoulder portion 246 of the hub 210 (see FIG. 17) is in contact with an inner surface 287 of the winged shield 212 (see FIG. 16), whereby the hub 210 is held by the winged shield 212.

FIGS. 19 to 20B show another example of the conventional medical needle device. The medical needle device shown in FIGS. 19 to 20B is constituted by a rigid needle 100, a hub 200, a tube 300 and a shield tube 400 that stores the hub 200 therein such that it can hold the hub 200. The shield tube 400 is provided with a wing 500 on its front end side. The hub 200 can slide in an axial direction inside the shield tube 400. As shown in FIG. 19, when a predetermined length of the rigid needle 100 protrudes from a front end of the shield tube 400, if a hook 222 of an engagement arm 211 is engaged with an engagement hole 410 of the shield tube 400, the sliding of the hub 200 toward a rear end side of the shield tube 400 is inhibited. After the use, by pinching the engagement arm 211 with fingers, the engagement is released, and the hub 200 is allowed to slide toward the rear end side of the shield tube 400. As shown in FIGS. 20A and 20B, an annular convex portion 220 collides with a step portion 420, thereby inhibiting the movement of the hub 200 toward the rear end side of the shield tube 400. At the same time, a base end side surface 231 of the annular groove 230 and a front end of a flexible abutting member 430 collide with each other, thereby the movement of the hub 200 toward the front end side of the shield tube 400 also is prevented. At this time, a cutting edge 111 of the rigid needle 100 is stored in the shield tube 400 completely (see, for example, Patent Document 2).

Patent Document 1: JP 5(1993)-503019 A
Patent Document 2: JP 10(1998)-85333 A

However, in the case where the hub 210 is held with the winged shield 212 by the engagement utilizing concave and convex shapes or a step, as the medical needle device described in Patent Document 1, adjustment of the holding force is limited. Since the above-described injection needle device is operated while holding the shield during a puncturing operation, it is necessary that the hub can be held securely with the shield and is integrated with the shield. Whereas, during a drawing operation for drawing the rigid needle into the shield after being used, it is preferable that the hub can slide easily inside the shield and the force for holding the hub by the shield is weak.

As described above, it is preferable that the holding force for storing the injection needle by the shield is set appropriately at the respective times of the puncturing operation and the drawing operation. However, in the conventional injection needle device that is explained above with reference to FIGS. 16 to 18, the hub is held by utilizing the concave and convex shapes, the step or the like, so that the appropriate holding force is not obtained at the respective times of the puncturing operation and the drawing.

On the other hand, the medical needle device described in Patent Document 2 can adjust the holding force at the respective times of the puncturing operation and the drawing operation to be more appropriate than the medical needle device described in Patent Document 1. However, since the hub 200 is provided with the engagement arm 211, the length of the hub 200 is increased accordingly. The medical needle device is sometimes fixed to a skin of a patient with an adhesive tape after the rigid needle punctures the patient, and thus preferably is as bendable as possible. However, the bendability of the hub is not taken into consideration. In most cases, the hub is formed by using a rigid material so as to secure the holding function by the shield, and it is almost impossible to bend the hub. Thus, it is preferable that a size of the hub is as small as possible.

These problems have been explained above by exemplifying the winged injection needle device that is provided with the rigid needle, but are common to a medical needle device further including a soft needle that is fixed to the front end portion of the shield and has an inner bore in which the rigid needle can be inserted, and a medical needle device having no wing. The above-described medical needle device that is provided with the soft needle particularly has a problem of a length of the hub. Since a part of the hub protrudes from the rear side of the shield in the state of storing the rigid needle into the shield, if the hub is long, the total length of the medical needle device is significantly long. If indwelling the soft needle in this state, a rear portion of the medical needle device is annoying.

The present invention provides a medical needle device that can hold a hub by a shield reliably during a puncturing operation, can allow the hub to slide easily inside the shield during a drawing operation, and is provided with a compact hub.

DISCLOSURE OF INVENTION

The medical needle device includes: a shield including a substantially cylindrical portion; a tube; a first hub that is inserted into an inner bore of the shield movably in an axial direction, whose rear end is connected with the tube; and a rigid needle that is fixed to a front end portion of the first hub; a hub movement controlling member that is attached to the shield detachably, wherein the hub movement controlling member includes: a stopper portion that is inserted from the rear end side of the shield into an inner bore of the shield exsertably, and has a front end that can be in contact with the first hub in a state of reaching a movement end on the front end side of the inner bore of the shield; and a holding portion that can maintain a state where a front end of the stopper portion is in contact with the first hub reaching the movement end on the front end side.

DESCRIPTION OF THE INVENTION

Figure 1:
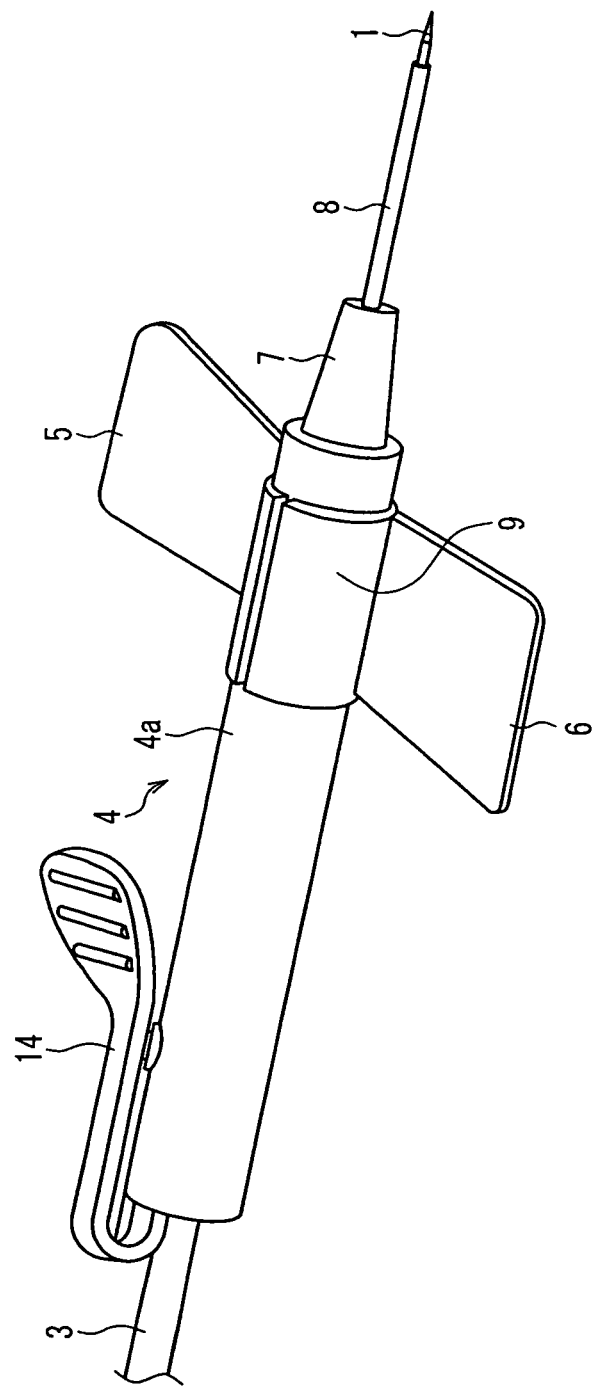
FIG. 1 is a perspective view of one example of a medical needle device of Embodiment 1 of the present invention.

Preferred embodiments of the present invention will be explained below.

An example of the medical needle device of the present invention may be a so-called "indwelling needle" including a soft needle that is fixed to the front end portion of the shield and has an inner bore in which the rigid needle can be inserted. In this case, the shield further includes a second hub that is fixed to a front end portion of the substantially cylindrical portion and constitutes a part of the shield. The soft needle is fixed to the second hub. And, a movement end on a front end side of the first hub in an inner bore of the shield is regulated by the second hub.

In one example of the medical needle device of the present invention, the shield further may include a pair of wing portions that are provided on the front end side of the substantially cylindrical portion. The pair of the wing portions may be fixed to the substantially cylindrical portion, or may be attachable/detachable with respect to the substantially cylindrical portion.

In one example of the medical needle device of the present invention, a hub movement controlling member includes, as a holding portion, a picking portion that is provided extending from a rear end of a stopper portion, has a surface opposing to an outer surface of the shield, and has a convex portion formed on the opposing surface. In this case, on the outer surface of the shield, a latching concave portion that corresponds to the convex portion is formed. The convex portion is fit with this latching concave portion, thereby maintaining a state where the front end of the stopper portion is in contact with the first hub that reaches a movement end on the front end side.

In one example of the medical needle device of the present invention, the hub movement controlling member includes a lever lock member as the holding portion. The lever lock member includes: a pair of pinching portions that respectively are provided with hook portions opposing to each other, and a cross-linking portion that cross-links the pair of the pinching portions and connects them with a rear end portion of the stopper portion. In this case, a pair of protruding portions that can be latched with the pair of the hook portions are formed on the outer surface of the shield. Each hook portion is latched with each protruding portion, thereby maintaining a state where the front end of the stopper portion is in contact with the first hub that reaches the movement end on the front end side in the inner bore of the shield.

In one example of the medical needle device of the present invention, the hub movement controlling member is provided with, as the holding portion, a pair of cantilever portions that are connected with the rear end portion of the stopper portion, and both of which are held from both sides by hand so as to decrease a distance therebetween for enabling the substantially cylindrical portion of the shield to be held. The pair of the cantilever portions are disposed around lateral portions of the substantially cylindrical portion for facilitating the puncturing operation, and preferably are disposed axisymmetrically, for example, symmetrically with each other with respect to a center line of the substantially cylindrical portion in its longitudinal direction. In this case, the upper-side outer surface of the substantially cylindrical portion is exposed. By applying fingers to this upper-side outer surface directly so as to press the substantially cylindrical portion toward the patient side, it is possible to facilitate the operation for pulling the tube and drawing the rigid needle into the shield.

In the case where the shield is provided with the pair of the wing portions that are attached to the front end side of the substantially cylindrical portion, it is preferable that a part of each cantilever portion is disposed at the same position in an axial direction of the substantially cylindrical portion as that of each wing portion. In this case, when lifting the pair of the wing portions upwards along the outer surface of the substantially cylindrical portion, superposing and holding them firmly, each cantilever portion is held so as to be sandwiched firmly between the wing portion and the substantially cylindrical portion of the shield. Thereby, it is possible to maintain the state where the front end of the stopper portion is in contact with the first hub that reaches the movement end on the front end side, for example, even by one hand, thereby performing the puncturing operation stably. Moreover, since the holding force between the wing portion and the substantially cylindrical portion can be adjusted by one hand, the maintenance by the hub movement controlling member in the state where the front end of the stopper portion is in contact with the first hub and the release of the maintenance can be performed by just one hand, so that the operability is excellent. It is preferable, if the protrusion is formed on the outer surface of the part of each cantilever portion at the same position in the axial direction of the substantially cylindrical portion as that of each wing portion, each cantilever portion is pinched more firmly between the wing portion and the substantially cylindrical portion of the shield, so that the puncturing operation can be performed stably.

Moreover, it is more preferable that each cantilever portion is provided with a convex portion for making contact with the wing, which is disposed at a position on the front end side with respect to the wing portion and protrudes toward the lateral direction. In this case, when holding the pair of the wing portions as described above, if a force is applied to the hub movement controlling member so as to slide it backwards, the convex portion for making contact with the wing is hooked by the wing portion. Thereby, the hub movement controlling member can be prevented from moving backwards. Thus, if each cantilever portion is provided with the convex portion for making contact with the wing, the hub movement controlling member can be prevented from moving backwards more reliably during the puncturing operation.

In one example of the medical needle device of the present invention, the first hub has a lateral penetration path that is formed to pierce from a circumference of the first hub to the inner bore thereof. Thereby, the space formed between the outer surface of the first hub and an inner surface of the shield is connected with the inner bore of the first hub via the lateral penetration path. Moreover, the first hub is provided with a sealing portion for keeping a liquid tightness between the outer surface of the first hub and the inner surface of the shield, at a position on the rear end side with respect to the lateral penetration path. This sealing portion is constituted of an annular groove and a sealing member that is disposed in the annular groove, for example. The sealing member may be an O-ring that is attached to the annular groove, and may be formed in the annular groove by coinjection molding or insertion formation.

In one example of the medical needle device of the present invention, an annular latching convex portion is provided on the inner surface of the shield. A movement end on the rear end side of the first hub in the inner bore of the shield is regulated by this annular latching convex portion. Whereas, the first hub is provided with a first large diameter portion and a second large diameter portion that are formed by the formation of the annular groove, and a large diameter portion having a bendable piece whose first end is supported by a third large diameter portion, in this order from the front end side. In such a medical needle device, the holding by the holding portion in the state where the front end of the stopper portion is in contact with the first hub is released, and the first hub moves toward the rear end side of the shield until the large diameter portion having the bendable piece passes over the annular latching convex portion, then the annular latching convex portion is disposed between the second large diameter portion and the large diameter portion having the bendable piece. Thereby, the rigid needle is drawn into the inner bore of the shield completely, so that the front end of the rigid needle is disposed in the inner bore of the shield, and the first hub is held by the shield such that the first hub does not move in the axial direction inside the shield. In this example, it is more preferable that, in the state where the annular latching convex portion is disposed between the second large diameter portion and the large diameter portion having the bendable piece, a side window for enabling visual recognition of the bendable piece from an outside of the shield is formed in the shield.

In one example of the medical needle device of the present invention, it is preferable that the large diameter portion having the bendable piece is provided with a plurality of the bendable pieces. In this case, it is more preferable that the plurality of the bendable pieces are arranged symmetrically with each other with respect to the center line of the first hub in its longitudinal direction, because the first hub can be held by the shield stably.

In one example of the medical needle device of the present invention, it is preferable that, in the state where the annular latching convex portion is disposed between the second large diameter portion and the large diameter portion having the bendable piece, the first hub is stored in the shield. When the first hub is stored in the shield as described above, it can suppress a risk that some power is applied to the first hub, the bendable piece-is bent toward a central axis of the first hub, and the first hub is drawn toward the front end side of the shield.

In one example of the medical needle device of the present invention, the first hub is provided with the first large diameter portion and the second large diameter portion that are formed by the formation of the annular groove that constitutes the sealing portion, and the large diameter portion having the bendable piece whose first end is supported by the third large diameter portion, in this order from the front end side. An inner diameter of the rear end portion of the shield is smaller than an inner diameter of the shield on a front end side with respect to the front end portion, and this rear end portion has a through hole that is formed to pierce the rear end portion from the outer surface of the substantially cylindrical portion to the inner bore of the substantially cylindrical portion is formed. In such a medical needle device, the holding by the holding portion in the state where the front end of the stopper portion is in contact with the first hub is released, and the first hub moves toward the rear end side of the shield, then a part of the bendable piece is disposed in the through hole. Thereby, the rigid needle is drawn into the shield completely, so that the front end of the rigid needle is disposed inside the shield, and the first hub is held by the shield so as not to move in the axial direction inside the shield.

In one example of the medical needle device of the present invention, the first hub is provided with the first large diameter portion and the second large diameter portion that are formed by the formation of the annular groove constituting the sealing portion, and a fourth large diameter portion, in this order from the front end side. Thus, an annular concave portion is formed between the second large diameter portion and the fourth large diameter portion. Since this first hub has a high strength but has a large contact area with the shield when the first hub 21 slides in contact with an inner surface of the shield, movement resistance of the first hub becomes large. Therefore, it is preferable that the substantially cylindrical portion of the shield is provided with a plurality of partition walls, by dividing the rear end portion of the substantially cylindrical portion into plural parts along its circumferential direction, and a protrusion that can be latched with the annular concave portion is formed on an inner surface of at least one of the partition walls. If the rear end portion of the substantially cylindrical portion is divided into the plural parts as described above, the first hub can move smoothly toward the rear end side of the shield. It is preferable that an outer diameter of the fourth large diameter portion becomes gradually smaller from its front end to its rear end. In this case, the fourth large diameter portion can pass over the protrusion of the partition wall more smoothly.

In one example of the medical needle device of the present invention, the annular latching convex portion is provided on the inner surface of the shield. The first hub is provided with the first large diameter portion and the second large diameter portion that are formed by the formation of the annular groove constituting the sealing portion, and a connecting portion that is connected with a tube, in this order from the front end side. The first hub further is provided with a plurality of the bendable pieces, each of which has first end supported by the second large diameter potion and is disposed away from the connecting portion around the connecting portion. On a surface of each bendable piece opposing to the inner surface of the shield, the groove that can be latched with the annular latching convex portion provided on the inner surface of the shield and is formed. The bendable piece having the groove functions as a means for holding the first hub such that it cannot move inside the shield after storing the needle, with the annular latching convex portion. In this medical needle device, the means for holding the first hub such that it cannot move inside the shield after storing the needle and the connecting portion are disposed at substantially the same position in the axial direction of the shield. Thus, the length of the first hub can be decreased, and the first hub can be compact. Thereby, the length of the shield also can be decreased.

In this medical needle device, the length of the shield preferably is set such that the first hub can be stored in the shield in the state where the annular latching convex portion is latched with the groove of the bendable piece having the groove. If the first hub is stored in the shield, it can suppress a risk that some force is applied to the first hub, the bendable piece is bent toward the central axis of the first hub, and the first hub is drawn toward the front end side of the shield.

The number of the bendable piece is not limited particularly as long as it is two or more, and may be selected appropriately according to a material of the bendable pieces, a height of the annular latching convex portion that is provided on the inner surface of the shield and the like. It is preferable that the plurality of the bendable pieces are arranged at an equal interval along the circumferential direction. In this case, the first hub can be held by the shield stably.

Embodiments of the present invention will be described specifically below with reference to the drawings.

Embodiment 1

Figure 2:
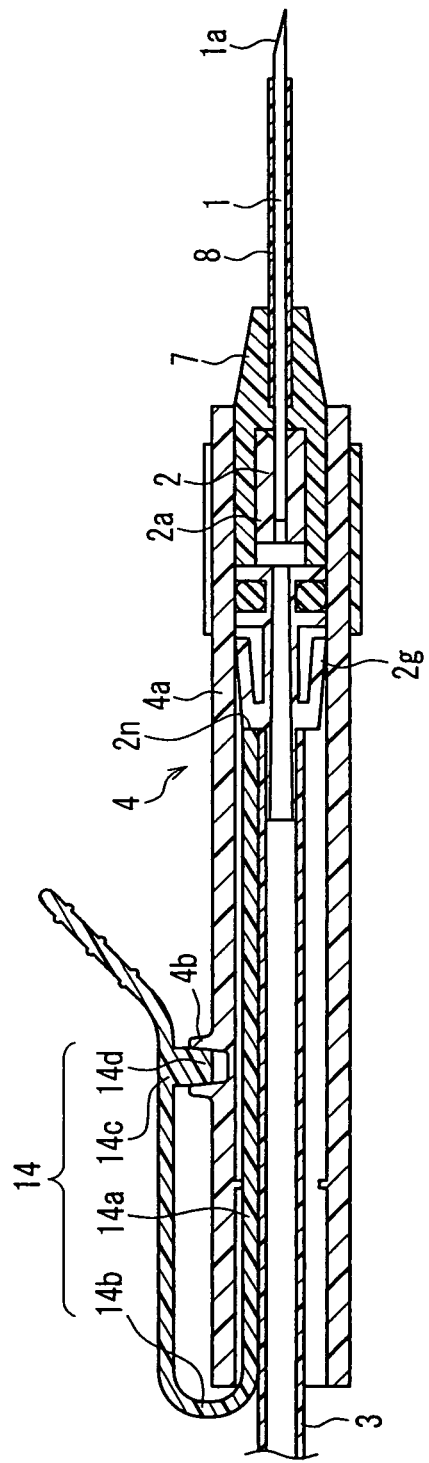
FIG. 2 is a cross-sectional view of the medical needle device shown in FIG. 1, which is cut in an axial direction.

FIG. 1 is a perspective view of one example of a medical needle device of Embodiment 1 of the present invention, and FIG. 2 is a cross-sectional view of the medical needle device shown in FIG. 1, which is cut in an axial direction.

In FIGS. 1 and 2, a rigid needle 1 made of a metal is fixed to a front end portion of a first hub 2 made of a resin. A tube 3 is connected with a rear end portion of the first hub 2. The winged shield 4 includes a substantially cylindrical portion 4a made of a resin, and left and right wing portions 5 and 6. The first hub 2 is inserted into an inner bore of the substantially cylindrical portion 4a and can move in an axial direction. The left and right wing portions 5 and 6 are provided at a front end portion of the substantially cylindrical portion 4a, that is, an end portion of the substantially cylindrical portion 4a on a side where a rigid needle protrudes. The pair of the wing portions 5 and 6 are attached, for example, to the substantially cylindrical portion 4a via a ring portion 9 that has a through slit in the same direction as the axial direction of the substantially cylindrical portion 4a, and has shapes that are symmetrical with each other with respect to the axis of the substantially cylindrical portion 4a. The ring portion 9 is attached to the substantially cylindrical portion 4a so as not to fall off, for example. To the shield 4, a hub movement controlling member 14 is attached detachably. Incidentally, FIG. 2 does not show a cross section of the rigid needle 1 for the convenience of the illustration. Also, FIGS. 4 to 6 do not show the cross section either.

As a material for the substantially cylindrical portion 4a, for example, polycarbonate, polypropylene and the like can be used. As a material for the wing portions 5 and 6, for example, soft polyvinyl chloride, polyethylene, polyolefin-based or polystyrene-based thermoplastic elastomer and the like can be used. As a material for the first hub 2, for example, polycarbonate, polypropylene and the like can be used. As a material for the hub movement controlling member 14, for example, polycarbonate, polypropylene, polyethylene and the like can be used.

A part of a second hub 7 is inserted into the front end portion of the substantially cylindrical portion 4a and is fixed thereto. The second hub 7 constitutes a part of the shield 4. A soft needle 8 is attached to an inner bore of the second hub 7 and is fixed thereto. The rigid needle 1 is inserted into an inner bore of the soft needle 8, and a tip of the rigid needle 1 protrudes from the soft needle 8. As a material for the second hub 7, for example, polycarbonate, polypropylene or the like is used, and as a material for the soft needle 8, for example, a polyurethane-based elastomer, a fluorocarbon resin such as polytetrafluoroethylene or the like is used.

Figure 3A:
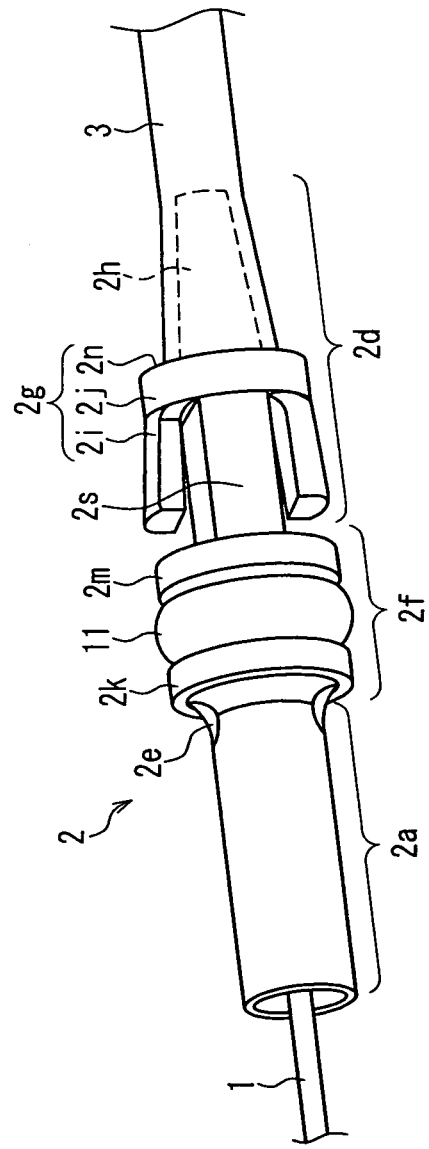
FIG. 3A is an enlarged perspective view of a first hub that constitutes the medical needle device shown in FIG. 1.
Figure 3B:
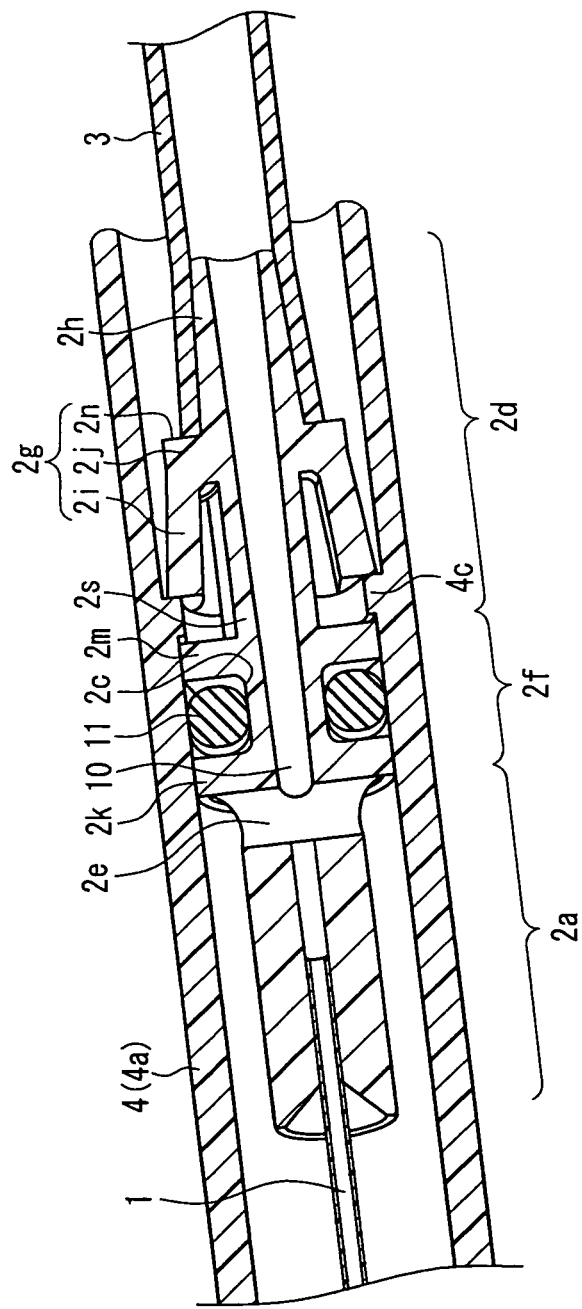
FIG. 3B is an enlarged cross-sectional view showing a latching structure for latching the first hub with a shield when a rigid needle that constitutes the medical needle device shown in FIG. 1 is stored into the shield.

FIG. 3A is an enlarged perspective view for explaining the first hub 2, and FIG. 3B is an enlarged cross-sectional view showing a latching structure for latching the first hub with the shield when the rigid needle is stored in the shield.

As shown in FIGS. 3A and 3B, the first hub 2 is constituted of the front end portion 2a, the rear end portion 2d, and a middle portion 2f that is positioned between the front end portion 2a and the rear end portion 2d. The rear end portion 2d includes: a large diameter portion 2g having a bendable piece, which is positioned near the middle portion 2f; and a connecting portion 2h that is positioned at a last end of the first hub, is inserted into an inner bore of a tube 3, and connects the first hub 2 and the tube 3. Thereby, the large diameter portion 2g having the bendable piece has an end surface 2n that faces an opening of the shield 4 on its rear end side. The rear end portion 2d also is provided with a connecting portion 2s that connects the large diameter portion 2g having the bendable piece and the middle portion 2f. The connecting portion 2h has a taper shape whose outer diameter decreases gradually from its front end to its rear end.

The middle portion 2f has an outer diameter that enables it to move easily in the inner bore of the substantially cylindrical portion 4a. The front end portion 2a has an outer diameter that is smaller than that of the middle portion 2f. Thereby, a space is formed between the inner surface of the substantially cylindrical portion 4a and the front end portion 2a as described below. The inner bore 10 at the middle portion 2f and the rear end portion 2d are set to have diameters that are larger than an inner diameter of the rigid needle 1.

The middle portion 2f of the first hub 2 is provided with an annular groove 2c for sealing, and an O-ring 11 is attached to an inside of this annular groove 2c so as to form a sealing portion. With this sealing portion, a liquid tightness between the outer surface of the first hub 2 and the inner surface of the substantially cylindrical portion 4a is maintained. Moreover, on both sides of the annular groove 2c, a first large diameter portion 2k and a second large diameter portion 2m that are formed by the formation of the annular groove 2c are formed in this order from the front end side of the first hub 2. Both of the first large diameter portion 2k and the second large diameter portion 2m have annular outer shapes, for example. On the middle portion 2f side of the front end portion 2a, a lateral penetration path 2e is formed. Thereby, a space formed between the outer surface of the first hub 2 and the inner surface of the substantially cylindrical portion 4a is connected with the inner bore 10 of the first hub 2 via this lateral penetration path 2e.

The large diameter portion 2g having the bendable piece is constituted of a pair of bendable pieces 2i and a third large diameter portion 2j that supports first ends of the bendable pieces 2i. If an outer diameter of the third large diameter portion 2j is equal to or slightly smaller than an inner bore diameter of the substantially cylindrical portion 4a at a position where an annular latching convex portion 4c is located, it is possible to secure easily an area for allowing a stopper portion 14a (see FIG. 2) of the below-described hub movement controlling member 14 to be in contact, and allow the third large diameter portion 2j to slide toward the rear end side of the shield 4 easily.

As shown in FIG. 2, the hub movement controlling member 14 is provided with the stopper portion 14a that can be inserted into the shield 4 from the rear end side of the shield 4 and can be exserted therefrom. The stopper portion 14a has a length that allows its front end to be in contact with the end surface 2n of the large diameter portion having the bendable piece in a state where the first hub 2 reaches the movement end on the front end side of the inner bore of the shield 4, as shown in FIG. 2.

The stopper portion 14a has a bar shape whose cross section is, for example, rectangular, arc or the like, and preferably has a flat end surface that can be in contact with the end surface 2n of the rear end portion of the first hub 2. An area of this end surface is set such that the stopper portion 14a can be in contact with the end surface 2n of the rear end portion of the first hub 2 reliably.

To the rear end portion of the stopper portion 14a, a picking portion 14c is connected via a curved part 14b. The picking portion 14c has a surface opposing to the outer surface of the shield 4, and a convex portion 14d is formed on this surface. On the outer surface of the shield 4, a latching concave portion 4b corresponding to the convex portion 14d is formed.

In the state shown in FIG. 2, the front end of the stopper portion 14a is in contact with the end surface 2n of the rear end portion of the first hub 2, and the convex portion 14d of the hub movement controlling member 14 fits with the latching concave portion 4b on the outer surface of the shield 4. An outer diameter of the front end portion 2a of the first hub 2 is slightly smaller than a diameter of the inner bore of the second hub 7 on its rear side, and the front end portion 2a is inserted into the inner bore of the second hub 7 on its rear side. The rigid needle 1 is in an initial state where its tip protrudes from the soft needle 8 such that it can puncture. Since the first hub 2 can be rotated around a central axis of the first hub 2 in the substantially cylindrical portion 4a, an opening of the tip 1a of the rigid needle 1 can be disposed in a predetermined direction before the rigid needle 1 punctures the skin of a patient.

Since the initial state can be maintained by fitting the convex portion 14d of the hub movement controlling member 14 with the latching concave portion 4b of the shield 4, it is not necessary that the first hub 2 be provided with a means for maintaining the initial state. Thus, the first hub 2 is shorter and more compact than, for example, a conventional hub that has a means for maintaining the initial state on its rear end side and has a means for holding the first hub 2 by the shield 4 on its front end side such that the first hub 2 can not move after storing the needle. Thus, during indwelling of the rigid needle 8, the medical needle device can be bent at a position that is sufficiently close to the rear end portion of the shield 4.

Figure 4:
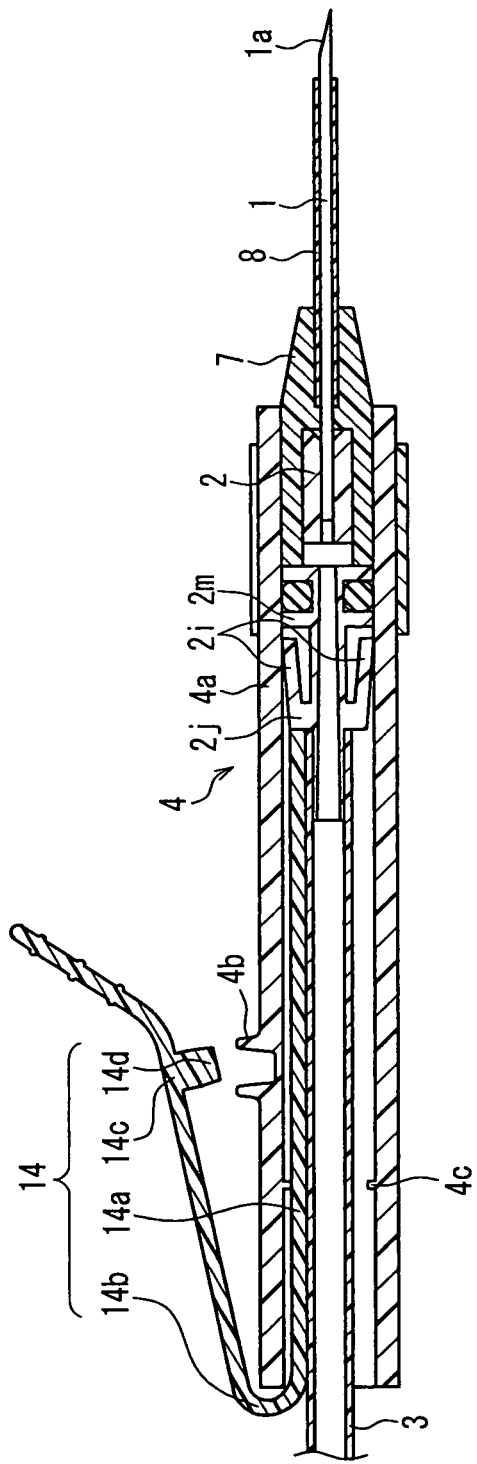
FIG. 4 is a cross-sectional view of the medical needle device shown in FIG. 1, which is cut in the axial direction, in a state of releasing engagement of a convex portion of a hub movement controlling member with a latching concave portion of the shield.
Figure 5:
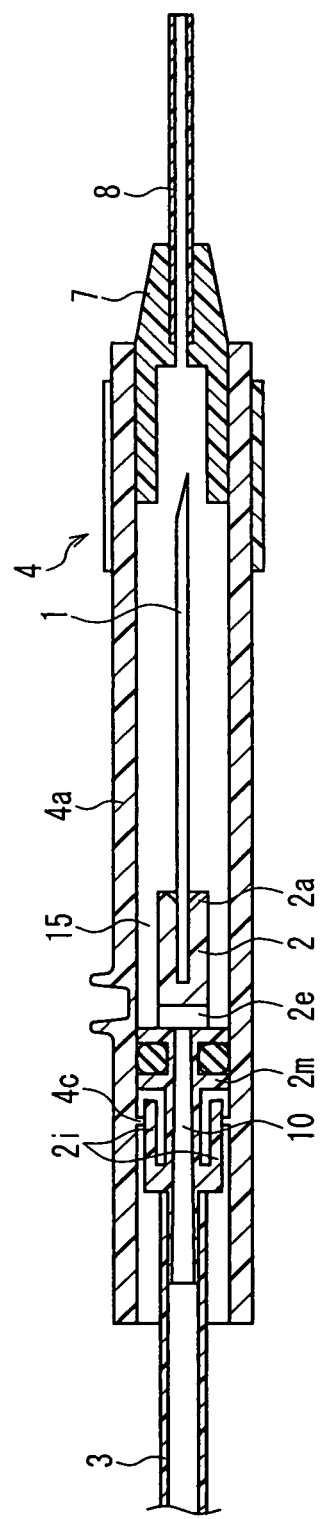
FIG. 5 is a cross-sectional view of the medical needle device shown in FIG. 1, which is cut in the axial direction, while sliding the first hub toward a rear end portion side of a substantially cylindrical portion.

After puncturing in this initial state, as shown in FIG. 4, the fitting of the convex portion 14d with the latching concave portion 4b is released, so that the hub movement controlling member 14 is exserted from the shield 4, and the rigid needle 1 is drawn into the shield 4. The third large diameter portion 2*j* has an outer diameter that is slightly smaller than, for example, the inner bore diameter of the substantially cylindrical portion 4*a* at the position where the annular latching convex portion 4*c* is located, and thus can pass over the annular latching convex portion 4*c* smoothly. Front ends of the pair of the bendable pieces 2*i* are almost in contact with the inner surface of the substantially cylindrical portion 4*a* at a position on the front end side with respect to the annular latching convex portion 4*c*. Thus, as shown in FIG. 5, both of the pair of the bendable pieces 2*i* are bent inwardly when passing over the annular latching convex portion 4*c*. However, each of the bendable pieces 2*i* is inclined from its front end side to its base end side such that a distance from the inner surface of the substantially cylindrical portion 4*a* is increased gradually (see FIG. 4), and thus can pass over the annular latching convex portion 4*c* smoothly. After passing over the annular latching convex portion 4*c*, each of the bendable pieces 2*i* is urged to be restored to its original state. Thus, the annular latching convex portion 4*c* is disposed between the large diameter portion 2*g* having the bendable piece, which includes the bendable piece 2*i*, and the second large diameter portion 2*m* (see FIG. 6).

Figure 6:
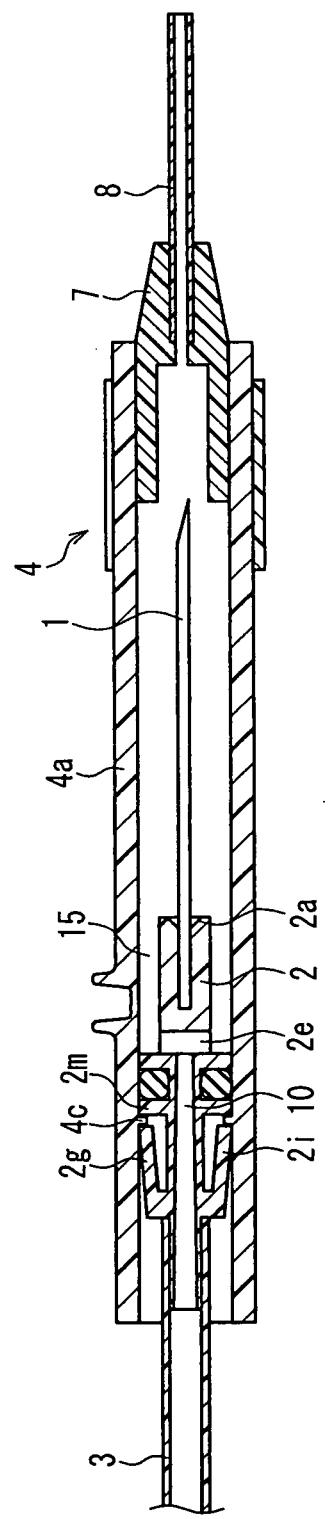
FIG. 6 is a cross-sectional view of the medical needle device shown in FIG. 1, which is cut in the axial direction, in a state where a bendable piece passes over an annular latching convex portion.

When the annular latching convex portion 4*c* is disposed between the large diameter portion 2*g* having the bendable piece and the second large diameter portion 2*m* as shown in FIG. 6, the further movement of the first hub 2 toward the rear end side of the shield 4 and the movement thereof in the reverse direction (toward the front end side of the shield 4) are inhibited. When the first hub 2 is pulled toward the rear end side of the shield 4 in this state, the second large diameter portion 2*m* is in contact with a step portion of the annular latching convex portion 4*c* on its front end side, thereby inhibiting the movement of the first hub 2 toward the rear end side of the shield 4. Thus, it is possible to prevent first hub 2 from disengaging from the shield 4 due to the force applied via a tube 3.

Whereas, when a force in a direction for re-protruding the rigid needle 1 is applied to the first hub 2, front end surfaces of the bendable pieces 2*i* are in contact with the step portion of the annular latching convex portion 4*c* on its rear end side, thereby inhibiting the movement of the first hub 2 toward the front end side of the shield 4 and the re-protrusion of the rigid needle 1. Since the pair of the bendable pieces 2*i* are arranged symmetrically with each other with respect to a center line of the first hub 2 in its longitudinal direction, the first hub 2 is held stably by the shield 4.

In the state shown in FIGS. 5 and 6, the front end portion 2*a* of the first hub 2 is out of the second hub 7, so that a space 15 is formed between the outer surface of the front end portion 2*a* with the smaller diameter and the inner surface of the substantially cylindrical portion 4*a* of the shield 4. The space 15 between the outer surface of the front end portion 2*a* and the inner surface of the substantially cylindrical portion 4*a* is connected with the inner bore 10 of the middle portion of the first hub 2 via the lateral penetration path 2*e*. The medical needle device of the present embodiment may indwell in a patient in the state shown in FIG. 6. Thereby, the space 15 formed between the outer surface of the first hub 2 and the inner surface of the substantially cylindrical portion 4*a* functions as a flow path to be added to a flow path that is formed by the inner bore of the rigid needle 1, so that a larger flow amount can be secured. Further, since the inner bore 10 of the first hub 2 has a diameter larger than that of the inner bore of the rigid needle 1, so that a larger flow amount can be secured in total, compared with that of a flow amount of the inner bore of the rigid needle 1 alone.

FIG. 3B is an enlarged cross-sectional view showing a structure of the first hub 2. According to this figure, a structure that a space between the outer surface of the front end portion 2*a* and the inner surface of the substantially cylindrical portion 4*a* of the shield is connected with the inner bore 10 in the middle portion of the first hub 2 via the lateral penetration path 2*e* can be recognized well. Thereby, a large flow amount can be secured as an additional flow path.

Incidentally, the picking portion 14*c* of the medical needle device of the present embodiment may be provided with a concave portion instead of the convex portion 14*d*. In this case, on the outer surface of the shield 4, a latching convex portion that corresponds to the above-described concave portion may be formed instead of the latching concave portion 4*b* (see FIG. 2 and the like).

Next, a method for using the medical needle device of the present embodiment will be explained.

Generally, the medical needle device of the present embodiment is used in the state shown in FIG. 2. In this initial state, the stopper portion 14*a* constituting the hub movement controlling member 14 is in contact with the end surface 2*n* of the rear end portion of the first hub 2, and the convex portion 14*d* of the hub movement controlling member 14 is fit with the latching concave portion 4*b* of the shield 4, as described above, so that the first hub 2 is held by the shield 4 so as not to move inside the shield 4. This holding force is at a level such that the rigid needle 1 does not slide backwards easily, and can be adjusted appropriately by adjusting shapes and the like of the convex portion 14*d* and the latching concave portion 4*b*.

The puncturing operation is performed, for example, by lifting the wing portions 5 and 6 upwards along the outer surface of the substantially cylindrical portion 4*a*, superposing and holding them (see FIG. 1).

In order to indwell the soft needle 8 after the puncturing, the first hub 2 is drawn into the inside of the substantially cylindrical portion 4*a* by an operation via the tube 3 so as to be in the state shown in FIG. 6. The fitting of the convex portion 14*d* of the hub movement controlling member 14 with the latching concave portion 4*b* of the shield 4 is released (see FIG. 4), the first hub 2 slides toward the rear end portion of the substantially cylindrical portion 4*a* (see FIG. 5), and the tube 3 is pulled until the bendable piece 2*i* passes over the annular latching convex portion 4*c* (see FIG. 6). The fitting of the convex portion 14*d* of the hub movement controlling member 14 with the latching concave portion 4*b* of the shield 4 can be released with almost no shaking of the rigid needle 1. Thus, it is possible to suppress vascular injury and slip-out of the soft needle 8 from an indwelling portion that can occur in accordance with the release of the fitting. Also, the above-described fitting can be released by one hand.

Since it can be recognized, by the sensation or a sound, that the bendable piece 2*i* passes over the annular latching convex portion 4*c*, there is no concern about poor holding of the first hub 2 by the shield 4. For example, in the case where the inner surface of the substantially cylindrical portion 4*a* is pressed by the bendable piece 2*i* on the inner surface of the substantially cylindrical portion 4*a* at a position on the front end side with respect to the annular latching convex portion 4*c*, a timing when the bendable piece 2*i* passes over the annular latching convex portion 4*c* can be realized more clearly. In this case, a pushing force of the bendable piece 2*i* may be set at a level that does not prevent the smooth sliding of the first hub 2.

As described above, the rigid needle 1 is exserted from a blood vessel, and only the soft needle 8 indwells. At this time, for example, if the first hub 2 is stored in the shield 4 as shown in FIG. 6, some force is applied to the first hub 2, and the bendable piece 2i is bent toward the central axis of the first hub 2, and as a result, the first hub 2 can be prevented from being drawn to the front end side of the shield 4. More preferably, the substantially cylindrical portion 4a of the shield 4 is made of, for example, a material with high transparency, because it can be recognized visually that the bendable piece 2i passes over the annular latching convex portion 4c. When disposing the medical needle device after the puncturing, a puncturing mistake can be prevented, if it is in the state shown in FIG. 6.

As described above, according to the medical needle device of the present embodiment, the holding force for holding the rigid needle 1 by the shield 4 can be set appropriately during the puncturing operation and a drawing operation and after storing the needle, respectively. That is, according to the medical needle device of the present embodiment, the first hub 2 can be held reliably by the shield 4 during the puncturing operation, the rigid needle 1 can move toward a storing position easily after the use, and after storing the rigid needle 1 at a position in the shield 4 that can prevent the puncturing, the state can be maintained reliably.

Embodiment 2

Figure 7:
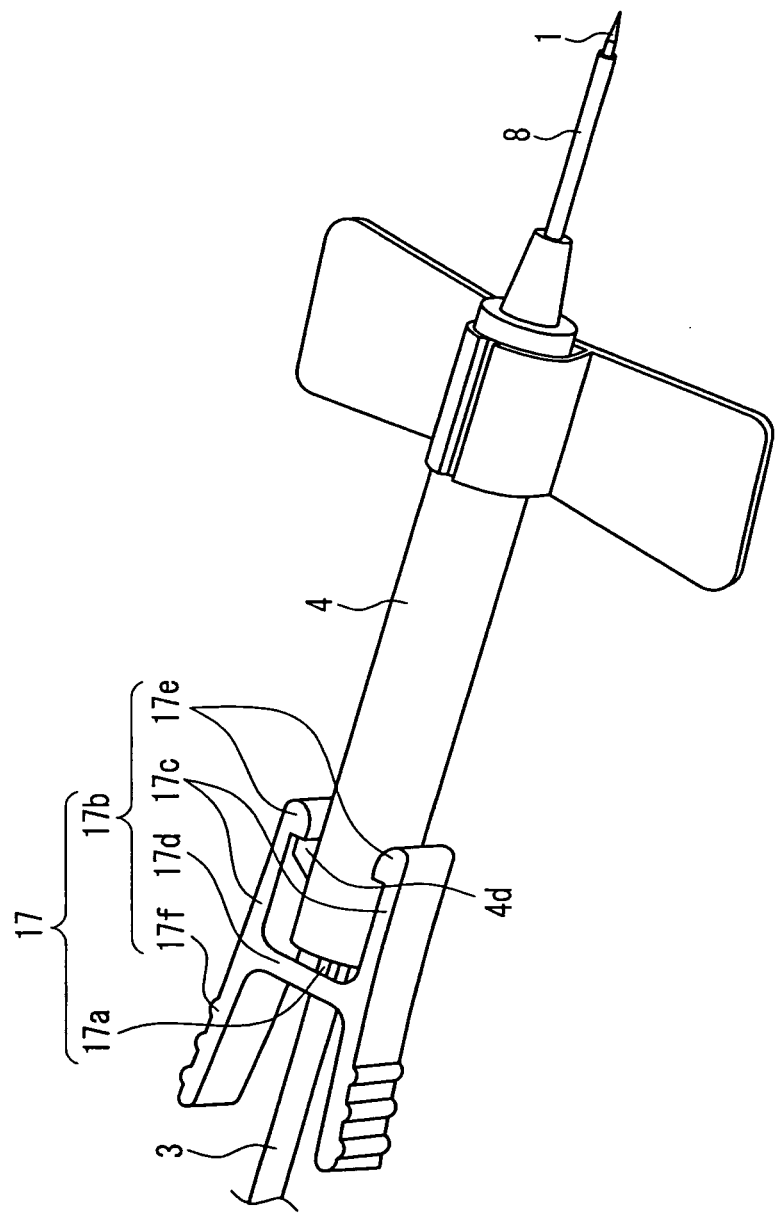
FIG. 7 is a perspective view showing one example of a medical needle device of Embodiment 2 of the present invention.

In Embodiment 2, another example of the medical needle device of the present invention will be explained. FIG. 7 is a perspective view showing one example of the medical needle device of Embodiment 2 of the present invention, and FIG. 8 is a cross-sectional view of the medical needle device shown in FIG. 7, which is cut in an axial direction.

Figure 8:
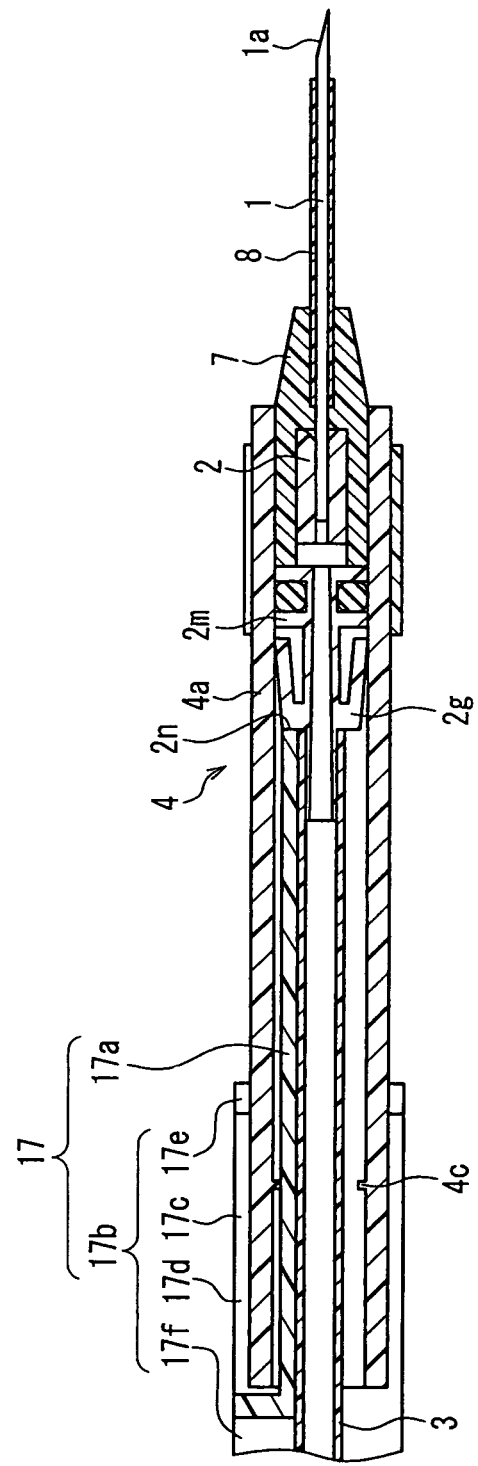
FIG. 8 is a cross-sectional view of the medical needle device shown in FIG. 7, which is cut in an axial direction.

A hub movement controlling member 17 of the medical needle device shown in FIGS. 7 and 8 has a shape different from that of the medical needle device of Embodiment 1.

As shown in FIGS. 7 and 8, the hub movement controlling member 17 in the medical needle device of the present embodiment is provided with a stopper portion 17a that can be inserted into the inner bore of the shield 4 from the rear end side of the shield 4 and can be exserted therefrom, and a lever lock member 17b. A front end of the stopper portion 17a can be in contact with the end surface 2n of the rear end portion of the first hub 2 that is inserted into the inner bore of a rear portion of the second hub 7 and reaches the movement end on the front end side. The lever lock member 17b functions as the holding portion for maintaining the state where the front end of the stopper portion 17a is in contact with the first hub 2 that reaches the movement end on the front end side. Incidentally, FIG. 8 does not show a cross section of the rigid needle 1 for the convenience of the illustration.

The lever lock member 17b is constituted of a pair of pinching portions 17c and a cross-linking portion 17d that cross-links the pair of the pinching portions 17c and connects them with a rear end portion of the stopper portion. A whole of the lever lock member 17b is made of, for example, a material having a property of being bent easily. When holding portions 17f of the pair of pinching portions 17c are held, connecting portions that connect the pinching portions 17c with the cross-linking portion 17d are bent so as to swing the pair of the pinching portions 17c. Thereby, according to the operation of the pair of the pinching portions 17c, the substantially cylindrical portion 4a of the shield 4 can be pinched/released.

At front ends of the pair of the pinching portions 17c, hook portions 17e are formed so as to oppose to each other. The pair of the hook portions 17e can be latched with a pair of protruding portions 4d that are formed on an outer surface of the substantially cylindrical portion 4a, in a state where the first hub 2 is in contact with the second hub 7 and reaches a movement end on the front end side, and the front end of the stopper portion 17a is in contact with the first hub 2. When each hook portion 17e is latched with each protruding portion 4d, the first hub 2 is held in the shield 4 so as not to move inside the shield 4. Thereby, the medical needle device can be in the usable initial state. Incidentally, shapes of the hook portions 17e and the protruding portions 4d are not limited particularly, as long as their latching is not released without picking the pair of the holding portions 17f.

In order to indwell only the soft needle 8 after the puncturing, the pair of the holding portions 17f firstly are picked so as to be close to each other, and the latching of each hook portion 17e with each protruding portion 4d is released. Next, after or while exserting the stopper portion 17a from the shield 4, the first hub 2 is drawn into the shield 4 by the operation via the tube 3. According to this operation, the annular latching convex portion 4c is disposed between the second large diameter portion 2m and the large diameter portion 2g having the bendable piece. Thereby, the rigid needle 1 is exserted from the blood vessel, and only the soft needle 8 is indwelled in the state of puncturing. The latching of each hook portion 17e with each protruding portion 4d may be released by moving the hub movement controlling member 17 backwards to the rear end side of the shield 4 while picking the pair of the pinching portions 17c, so that almost no shaking is provided to the rigid needle 1. Thus, it can suppress the vascular injury and the slip-out of the soft needle 8 from the indwelling portion, which may occur during the above-described releasing of the latching. Also, the latching can be released by one hand.

Except for the above, the medical needle device of the present embodiment has a structure and an effect that are similar to those of the medical needle device of Embodiment 1.

Embodiment 3

Figure 9A:
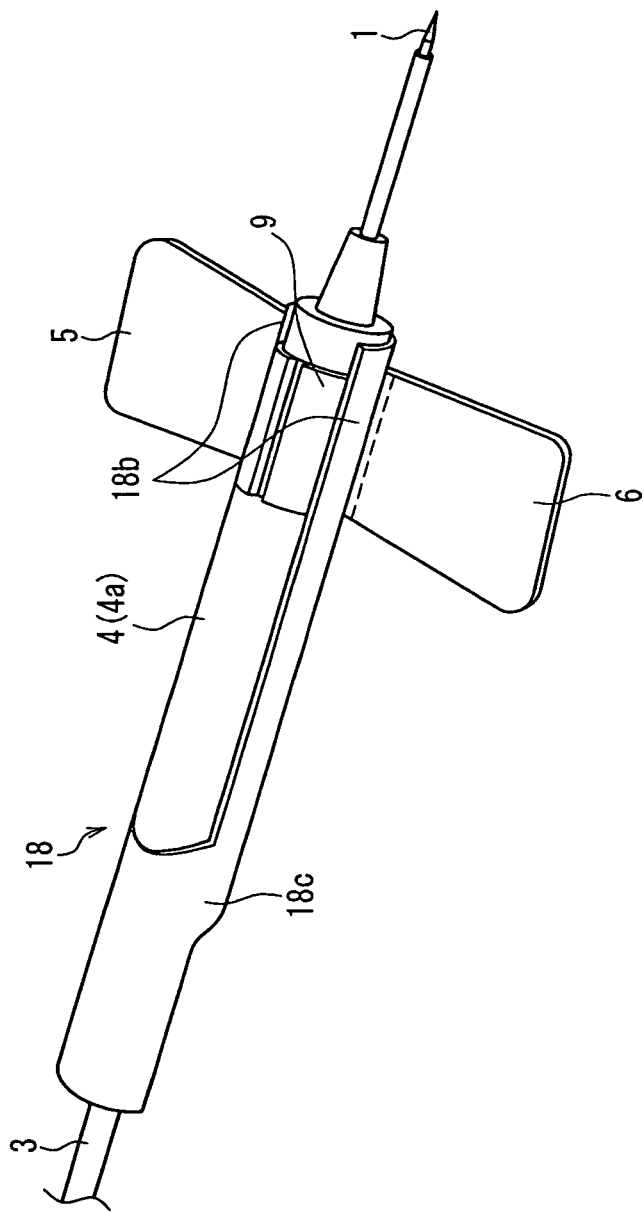
FIG. 9A is a perspective view showing one example of a medical needle device of Embodiment 3 of the present invention.
Figure 9B:
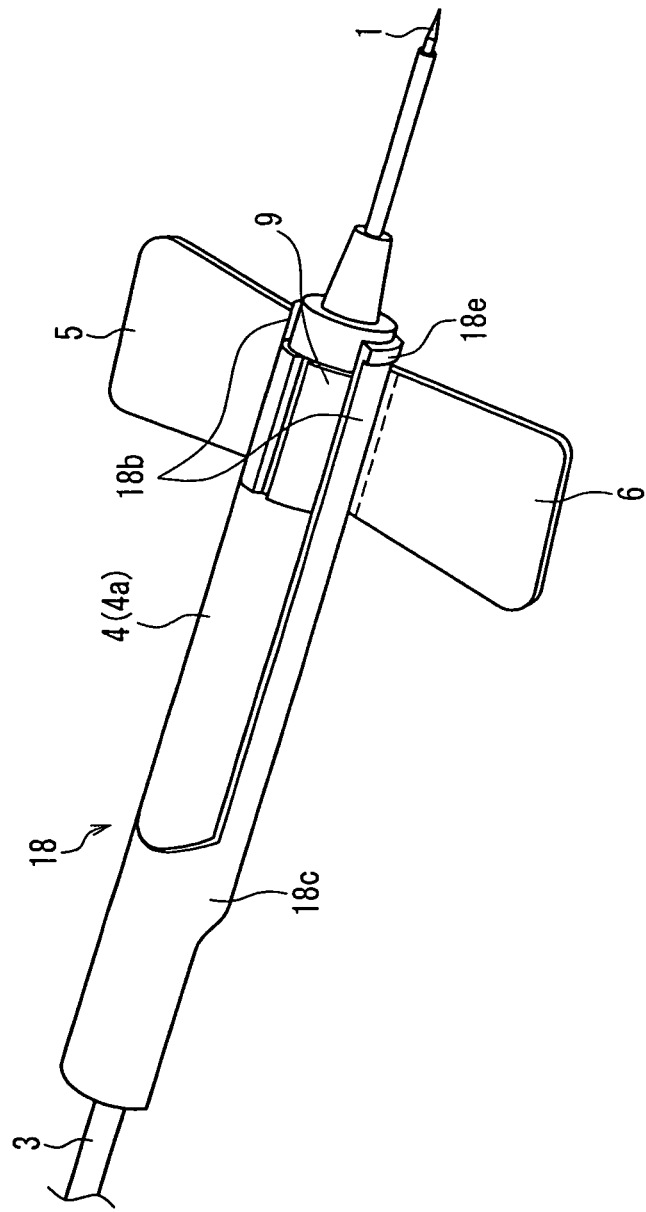
FIG. 9B is a perspective view showing another example of the medical needle device of Embodiment 3 of the present invention.
Figure 9C:
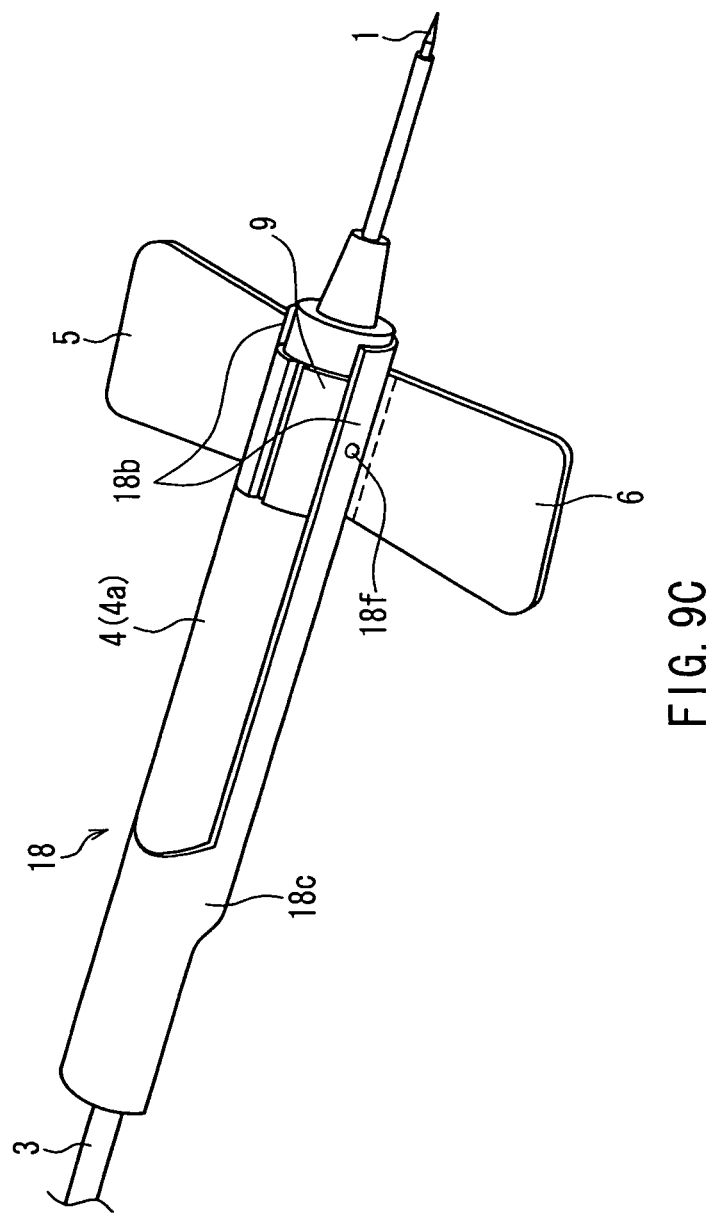
FIG. 9C is a perspective view showing still another example of the medical needle device of Embodiment 3 of the present invention.

In Embodiment 3, still another example of the medical needle device of the present invention will be explained. FIGS. 9A to 9C are perspective views showing one example of a medical needle device of the present embodiment, and FIG. 10 is a cross-sectional view of the medical needle device shown in FIGS. 9A to 9C, which is cut in an axial direction.

A hub movement controlling member 18 of the medical needle device shown in FIGS. 9A to 9C has a shape different from those of the medical needle devices of Embodiments 1 and 2.

Figure 10:
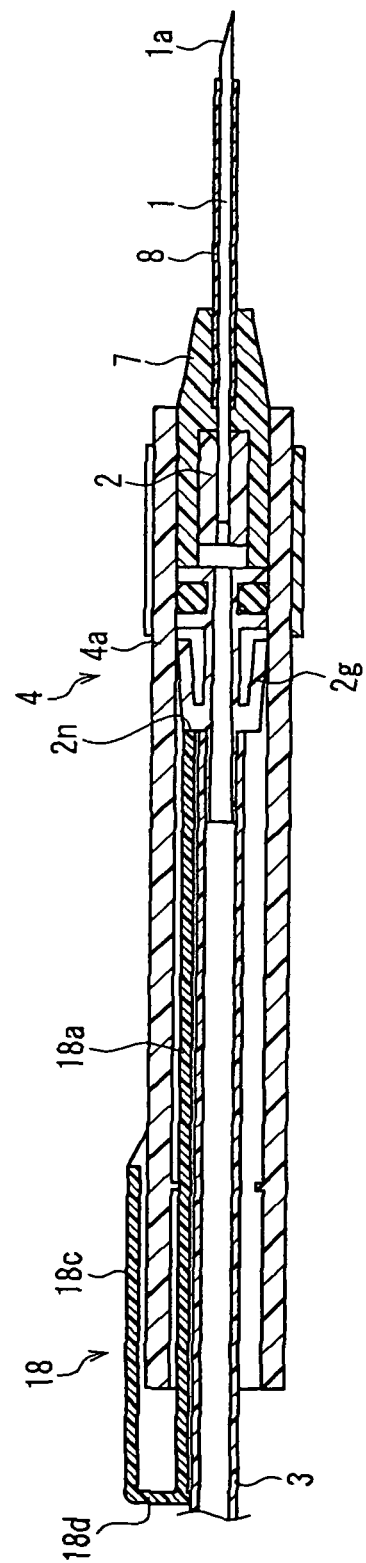
FIG. 10 is a cross-sectional view of the medical needle device shown in FIGS. 9A to 9C, which is cut in an axial direction.

As shown in FIGS. 9A to 10, the hub movement controlling member 18 of the medical needle device of the present embodiment is provided with the stopper portion 18a that can be inserted into the inner bore of the shield 4 from the rear end side of the shield 4 and can be exserted therefrom, and the holding portion having a shape described below. The holding portion having the below-described shape functions to maintain a state where the front end of the stopper portion 18a is in contact with the first hub 2 that reaches the movement end on the front end side. The front end of the stopper portion 18a can be in contact with the end surface 2n of the rear end portion of the first hub 2 that is inserted into the inner bore of a rear portion of the second hub 7 and reaches the movement end on the front end side. Incidentally, FIG. 10 does not show a cross section of the rigid needle 1 for the convenience of the illustration.

The hub movement controlling member 18 is provided with a pair of cantilever portions 18b as the holding portion. The pair of the cantilever portions 18b are connected with the rear end portion of the stopper portion 18*a* via a substantially semicylindrical portion 18*c* that covers a part of an upper-side circumference of the substantially cylindrical portion 4*a* of the shield 4, and a curved part 18*d*. The substantially semicylindrical portion 18*c* and the pair of the cantilever portions 18*b* are disposed at positions that are slightly away from the outer surface of the substantially cylindrical portion 4*a* of the shield 4. The pair of the cantilever portions 18*b* are disposed around lateral portions of the substantially cylindrical portion 4*a*, and are arranged symmetrically with each other with respect to the center line of the substantially cylindrical portion 4*a* in its longitudinal direction.

The pair of the cantilever portions 18*b* can be held from its both sides by hand so as to decrease a distance therebetween, so that the substantially cylindrical portion 4*a* of the shield 4 can be held. While holding the substantially cylindrical portion 4*a* by the pair of the cantilever portions 18*b*, a relative position of the hub movement controlling member 18 with respect to the shield 4 can be maintained without being changed. Thus, in a state where the first hub 2 is inserted into the inner bore of the second hub 2 and reaches the movement end on the front end side in the inner bore of the shield 4, when the front end of the stopper portion 18*a* is in contact with the end surface 2*n* of the large diameter portion 2*g* having the bendable piece and the shield 4 is held by the pair of the cantilever portions 18*b*, the movement of the first hub 2 can be prevented, so that the puncturing operation can be performed reliably.

In the case where, as shown in FIG. 9A, a part of each cantilever portion 18*b* is disposed at a position that is the same as a position of each of the wing portions 5 and 6 in the axial direction of the substantially cylindrical portion 4*a*, the puncturing operation can be performed by lifting the wing portions 5 and 6 upwards along the outer surface of the substantially cylindrical portion 4*a*, superposing and holding them by hand. Thus, each cantilever portion 18*b* can be held in a state of being fastened by each of the wing portions 5 and 6 and the ring portion 9, whereby the relative position of the hub movement controlling member 18 with respect to the shield 4 can be maintained without being changed, and thus the drawing of the needle can be prevented.

In the example shown in FIG. 9B, a convex portion 18*e* for making contact with the wing, which protrudes toward a lateral direction, is formed at a plate part that constitutes each cantilever portion 18*b* at a position on the front end side with respect to the wing portions 5 and 6. Thus, in the state where the pair of the wing portions 5 and 6 are lifted upwards along the outer surface of the substantially cylindrical portion 4*a* and are superposed, when a force for allowing the hub movement controlling member 18 to slide backwards is applied, the convex portion 18*e* for making contact with the wing is hooked by the wing portions 5 and 6, thereby inhibiting the backward movement of the hub movement controlling member 18. As described above, if each cantilever portion 18*b* is provided with the convex portion 18*e* for making contact with the wing, the backward movement of the hub movement controlling member 18 during the puncturing operation can be prevented more reliably.

In the example shown in FIG. 9C, a protrusion 18*f* is formed on an outside surface of each cantilever portion 18*b* at a position that is the same as the wing portion in the axial direction of the substantially cylindrical portion. Thus, if lifting the pair of the wing portions 5 and 6 upwards along the outer surface of the substantially cylindrical portion, superposing and holding them firmly, each cantilever portion is held to be sandwiched between the wing portion and the ring portion 9 more firmly. Moreover, similarly to the example shown in FIG. 9A, since the holding force power between each of the wing portions 5 and 6 and the ring portion 9 also can be adjusted by one hand, it is possible to perform, by one hand, the maintenance of the state where the front end of the stopper portion is in contact with the first hub by the hub movement controlling member 18 and the release of the maintenance, so that the operability thereof also is excellent.

Since each cantilever portion 18*b* is disposed around the lateral portion of the substantially cylindrical portion 4*a*, an upper-side part of the outer surface of the substantially cylindrical portion 4*a* is exposed. Thus, during its use, it is possible to apply fingers to the exposed outer surface of the substantially cylindrical portion 4*a* directly and press the substantially cylindrical portion 4*a* toward the patient side. This operation facilitates to pull the tube 3 so as to draw the rigid needle 1 into the shield 4.

In FIG. 10, the rigid needle 1 is in the initial state that protrudes from the soft needle 8 and can puncture. For maintaining this state, the stopper portion 18*a* shown in FIG. 10 is too long. However, if the rear end side of the stopper portion 18*a* protrudes from the rear end of the shield 4 as shown in FIG. 10, the protruding part and the tube 3 can be grasped by hand. Thus, if the stopper portion 18*a* is sufficiently long as shown in FIG. 10, it is possible to draw the rigid needle 1 into the shield 4 easily in a state of grasping the hub movement controlling member 18 and the tube 3 at the same time.

As shown in FIGS. 9A to 9C, break lines that enable to break the wing portions 5 and 6 apart from the shield 4 are formed in base end parts of the wing portions 5 and 6 in the medical needle device of the present embodiment. Thus, it also is possible to indwell the medical needle device in a patient, in a state where the wing portions 5 and 6 are broken away from the ring portion, that is, from the shield 4, after the puncturing operation.

Except for the above, the medical needle device of the present embodiment has a structure and an effect that are similar to those of the medical needle device of Embodiment 1.

Incidentally, the break lines formed in the base end parts of the wing portions 5 and 6 may be formed not only in the medical needle device of the present embodiment but also in the winged medical needle devices of other embodiments of the present invention.

Embodiment 4

Figure 11A:
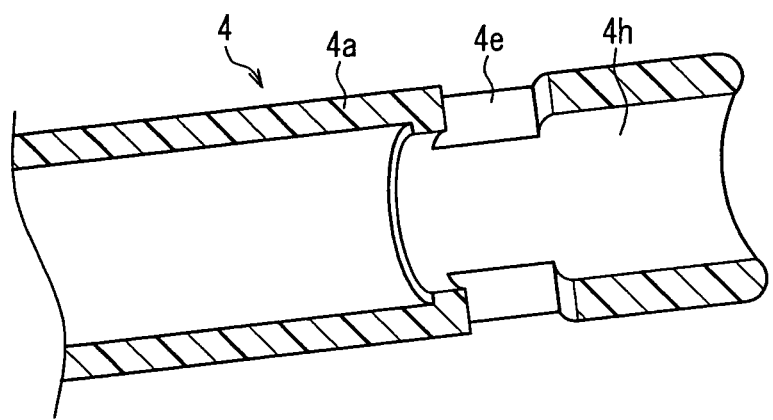
FIG. 11A is an enlarged cross-sectional view of a part of a shield that constitutes one example of a medical needle device of Embodiment 4 of the present invention.

In Embodiment 4, still another example of the medical needle device of the present invention will be explained. FIG. 11A is an enlarged cross-sectional view of a part of a shield that constitutes the medical needle device of Embodiment 4 of the present invention, and FIG. 11B is an enlarged cross-sectional view showing a latching structure for latching a first hub to a shield when a rigid needle is stored into the shield.

Figure 11B:
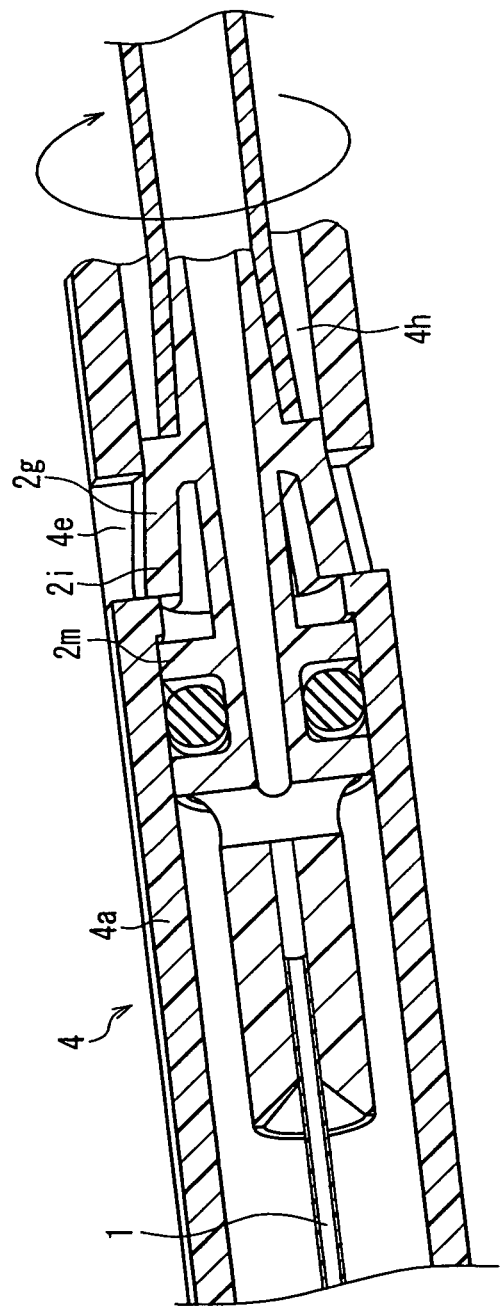
FIG. 11B is an enlarged cross-sectional view showing a latching structure for latching a first hub with a shield when a rigid needle that constitutes the medical needle device of Embodiment 4 of the present invention is stored into the shield.

As shown in FIGS. 11A and 11B, in the medical needle device of the present embodiment, an inner diameter of a rear end portion 4*h* of the shield 4 is smaller than an inner diameter thereof at a position on a front end side with respect to the rear end portion 4*h*. And, the rear end portion 4*h* has a through hole 4*e* that is formed to pierce from the outer surface of the substantially cylindrical portion 4*a* to the inner bore is formed. Except for the above, the medical needle device of the present embodiment has a structure and an effect that are similar to those of the medical needle device of Embodiment 1.

In such a medical needle device, when maintaining the state where the front end of the stopper portion is in contact with the first hub 2 is released and the first hub 2 moves toward the rear end side of the shield 4, the large diameter portion 2g having the bendable piece passes over a step portion that connects a part of the substantially cylindrical portion 4a whose inner diameter is relatively large and a part thereof whose inner diameter is small. If necessary, the first hub 2 is rotated around its central axis so as to match positions of the bendable piece 2i and the through hole 4e. Since a front end of the bendable piece 2i is pressed and pushed against an inner surface of the substantially cylindrical portion 4a at a position whose inner diameter is relatively small, a part of the bendable piece 2i is disposed inside the through hole 4e, by the operation of matching the positions of the bendable piece 2i and the through hole 4e. An end surface of the front end of the bendable piece 2i is in contact with a wall surface forming the through hole 4e. Thereby, the rigid needle 1 is drawn into the shield 4 completely, and a tip of the rigid needle 1 is disposed inside the shield 4. At the same time, the first hub 2 is held by the shield 4 so as not to move inside the shield 4. The matching of the positions of the bendable piece 2i and the through hole 4e can be recognized visually from the through hole 4e.

The matching of the positions of the bendable piece 2i and the through hole 4e may be performed by sliding the first hub 2 toward the rear end side of the shield 4 and thereafter rotating it, and also may be performed by sliding the first hub 2 while rotating it.

Embodiment 5

Figure 12:
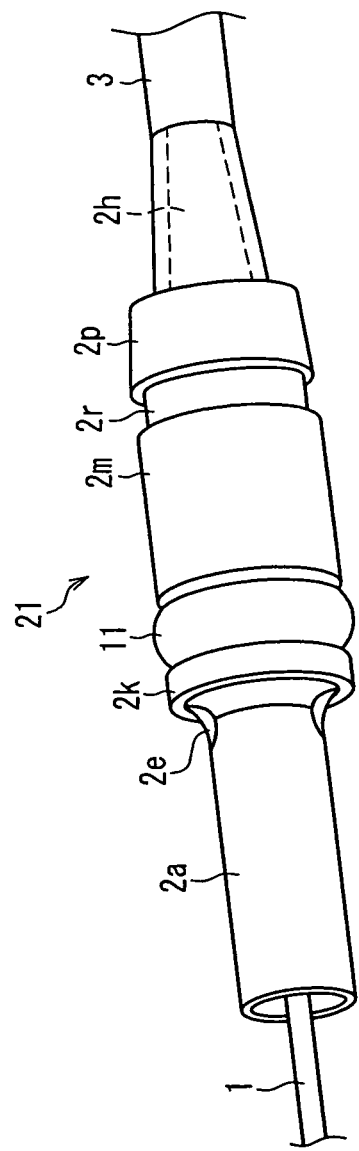
FIG. 12 is a perspective view of a first hub that constitutes one example of a medical needle device of Embodiment 5 of the present invention.
Figure 13A:
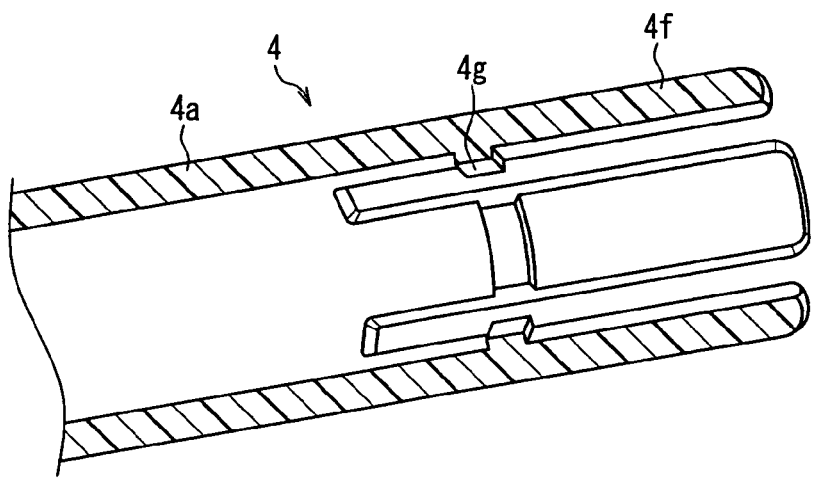
FIG. 13A is a cross-sectional view of a part of a shield that constitutes the medical needle device of Embodiment 5 of the present invention.
Figure 13B:
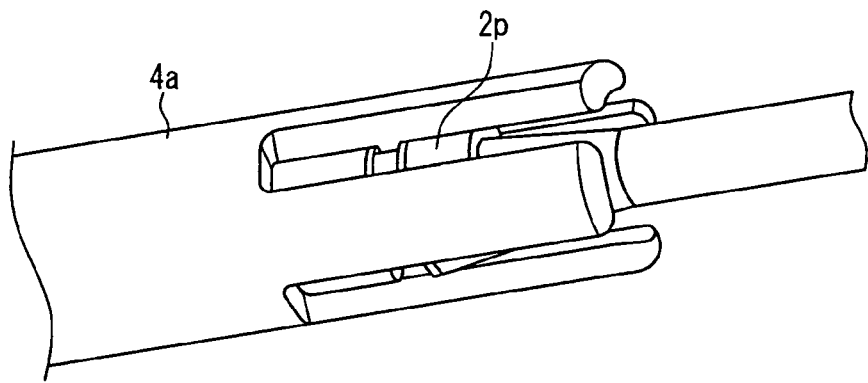
FIG. 13B is a perspective view showing a latching structure for latching the first hub with a shield when a rigid needle that constitutes the medical needle device of Embodiment 5 of the present invention is stored into the shield.
Figure 13C:
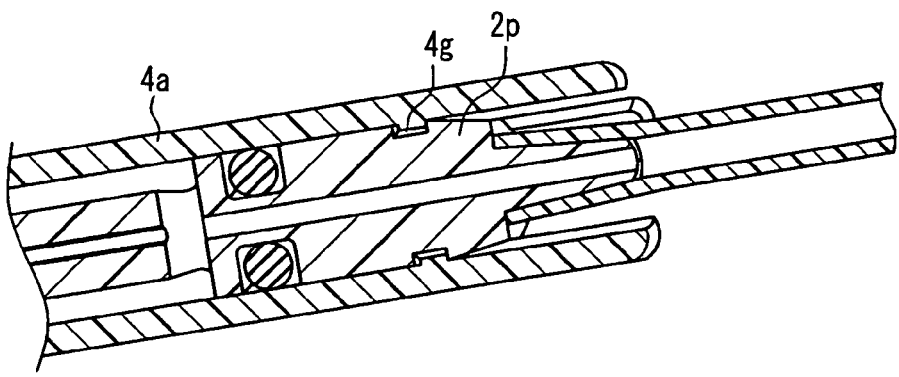
FIG. 13C is a cross-sectional view of FIG. 13B.

In Embodiment 5, still another example of the medical needle device of the present invention will be explained. FIG. 12 is a perspective view of a first hub that constitutes the medical needle device of the present embodiment of the present invention. FIG. 13A is a perspective cross-sectional view of a part of a shield, FIG. 13B is a perspective view showing a latching structure for latching the first hub to the shield when a rigid needle is stored into the shield, and FIG. 13C is a cross-sectional view of FIG. 13B.

The medical needle device of the present embodiment has a structure similar to that of the medical needle device of Embodiment 1, except that a latching structure for latching the first hub to the shield when storing the rigid needle into the shield is different from that of Embodiment 1, and has a similar effect.

In the present embodiment, as shown in FIG. 12, the first hub 21 is provided with an annular fourth large diameter portion 2p at its rear end portion, instead of the large diameter portion 2g having the bendable piece of Embodiment 1 (see FIG. 3A), and has an annular concave portion 2r between the second large diameter portion 2m and the fourth large diameter portion 2p. Other parts of the first hub 2 that are similar to those of Embodiment 1 are denoted by the same reference numerals as those of Embodiment 1, and the explanations thereof will be omitted.

As shown in FIG. 13A, the rear end portion of the substantially cylindrical portion 4a of the shield 4 is divided into plural parts along its circumferential direction so as to be provided with a plurality of partition walls 4f. On an inside surface of each partition wall 4f, a protrusion 4g that can be latched with the annular concave portion 2r (see FIG. 12) is formed.

The first hub 21 shown in FIG. 12 has a strength higher than that of the first hub used in Embodiment 1, but has higher movement resistance because of its large contact area with the shield when the first hub 21 slides in contact with an inner surface of the shield. However, as shown in FIGS. 13A to 13C, if the shield 4 is divided into the plural parts, when the fourth large diameter portion 2p of the first hub 2 passes over the protrusion 4g that is formed on the rear end portion side of the substantially cylindrical portion 4a, the partition walls 4f are bent outwardly. Thus, the first hub 2 can move smoothly toward the rear end side of the shield 4. Also, it can be recognized visually that the first hub 2 is held by the shield 4 so as not to move inside the shield.

As shown in FIG. 13C, the fourth large diameter portion 2p has a maximum outer diameter that is substantially equal to an inner bore diameter of the inside surface of the substantially cylindrical portion 4a at a position on the front end side with respect to the protrusion 4g. However, since the outer diameter of the fourth large diameter portion 2p is decreased gradually from its front end to its rear end, the fourth large diameter portion 2p can slide more smoothly over the protrusion 4g.

In the example show in FIG. 13A, the shield 4 is provided with the four partition walls 4f, but the number of the partition walls 4f is not limited particularly. Moreover, it is not necessary that all of the partition walls 4f are provided with the protrusions 4g. If the fourth large diameter portion 2p can pass over the protrusion 4g smoothly, and the movement of the first hub 2 into its axial direction after storing the rigid needle can be inhibited sufficiently, the protrusions 4g may be provided on, for example, the alternate partition walls 4f in the circumferential direction.

Embodiment 6

Figure 14A:
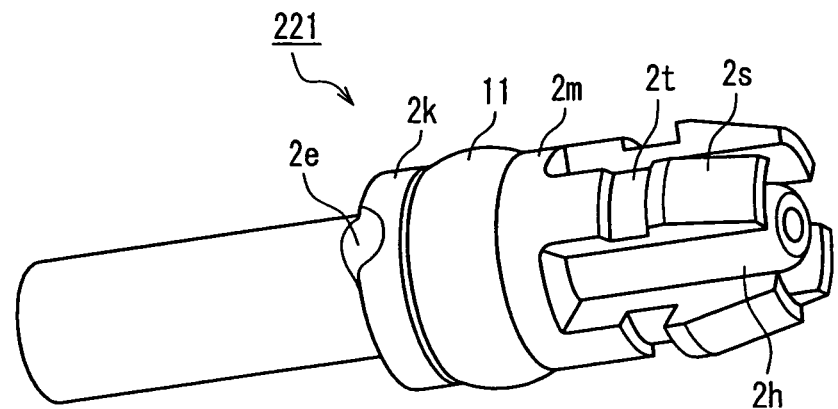
FIG. 14A is a perspective view of a first hub that constitutes the medical needle device of Embodiment 6 of the present invention.

In Embodiment 6, still another example of the medical needle device of the present invention will be explained. FIG. 14A is a perspective view of a first hub that constitutes the medical needle device of the present embodiment, and FIG. 14B is a cross-sectional view showing a latching structure for latching the first hub to a shield when a rigid needle is stored into the shield.

The medical needle device of the present embodiment has a structure and an effect that are similar to those of the medical needle device of Embodiment 1, except that a latching structure of the present embodiment for latching the first hub with the shield is different from that of Embodiment 1. In FIGS. 14A and 14B, parts that are similar to those of Embodiment 1 are denoted by the same reference numerals as those of Embodiment 1, and the explanations thereof will be omitted.

Figure 14B:
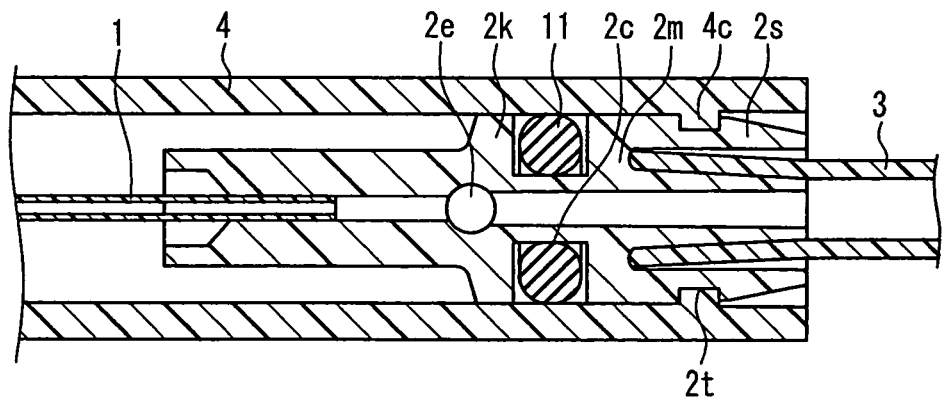
FIG. 14B is a cross-sectional view showing a latching structure for latching the first hub with a shield when a rigid needle that constitutes the medical needle device of Embodiment 6 of the present invention is stored into the shield.

As shown in FIGS. 14A and 14B, a first hub 221 is provided with the first large diameter portion 2k and the second large diameter portion 2m that are formed by the formation of the annular groove 2c, and the connecting portion 2h to be connected with the tube, in this order from the front end side. Also in the present embodiment, the O-ring 11 is attached between the first large diameter portion 2k and the second large diameter portion 2m so as to form the sealing portion similarly to the case of Embodiment 1. With this sealing portion, a liquid tightness between the outer surface of the first hub 221 and the inner surface of the shield 4 can be maintained.

On the rear end side with respect to the second large diameter portion 2m, there are a plurality of bendable pieces 2s, each of which has first end supported by the second large diameter portion 2m. These bendable pieces 2s are arranged concentrically with respect to the connecting portion 2h around the connecting portion 2h. The connecting portion 2h and each bendable piece 2s are positioned to have a distance that enables the tube 3 to be attached to the connecting portion 2h.

On a surface opposing to the inner surface of the shield 4 of each bendable piece 2s, a groove 2t that can be latched with the annular latching convex portion 4c on the inner surface of the shield 4 is formed. The bendable piece having the groove functions with the annular latching convex portion 4c, as a means for holding the first hub 221 to the shield 4 after storing the rigid needle 1 into the shield 4. As described above, if the means for holding the first hub 221 to the shield 4 immovably after storing the rigid needle and the connecting portion 2h are disposed at substantially the same position in the axial direction of the shield 4, the length of the first hub 221 in the axial direction can be short, and the first hub 221 can be compact. Thereby, the length of the shield 4 also can be short.

As shown in FIG. 14B, it is preferable that the length of the shield 4 is set such that the first hub 2 is stored in the shield 4 in the state where the annular latching convex portion 4c is engaged with the grooves 2t of the bendable pieces 2s. If the first hub 2 is stored in the shield 4 completely, it can suppress a risk that some force is applied to the first hub 221, the bendable piece 2s is bent toward the central axis of the first hub 2, and the first hub 221 is drawn toward the front end side of the shield 4.

The number of the bendable piece 2s may be two or more, which is not limited particularly, and may be determined appropriately according to the material of the bendable pieces 2s, the height of the annular latching convex portion 4c and the like. The plurality of the bendable pieces 2s preferably are arranged at an equal interval along the circumferential direction. This case is preferable because the first hub 2 can be held by the shield 4 stably.

Embodiment 7

Figure 15:
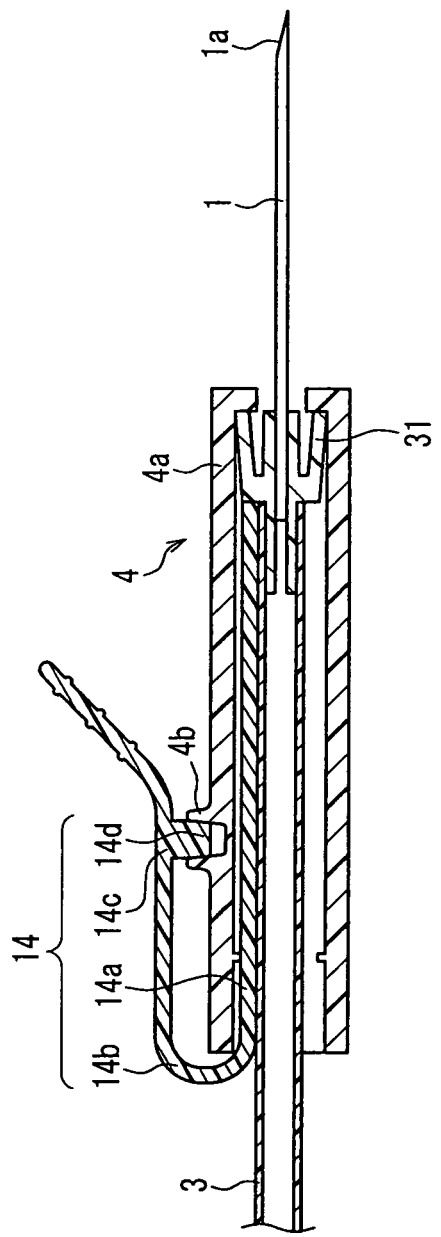
FIG. 15 is a cross-sectional view of one example of a medical needle device of Embodiment 7 of the present invention, which is cut in an axial direction.
Figure 16:
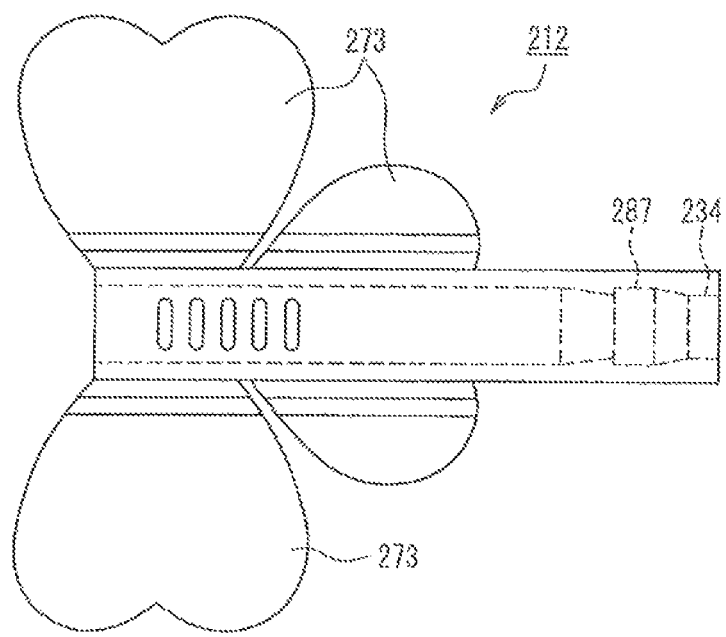
FIG. 16 is a plan view of a shield that constitutes one example of a conventional medical needle device.
Figure 17:
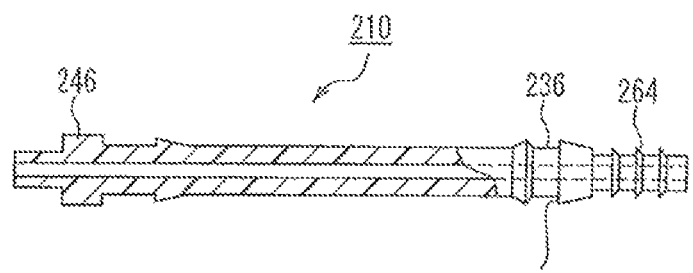
FIG. 17 is a partial cross-sectional view of a hub that constitutes one example of a conventional medical needle device.
Figure 18:
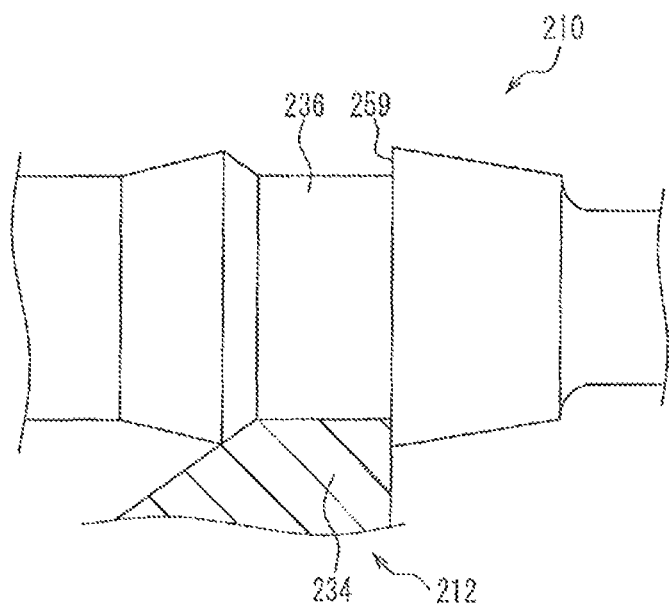
FIG. 18 is an enlarged cross-sectional view showing a state where the shield shown in FIG. 16 is engaged with the hub shown in FIG. 17.
Figure 19:
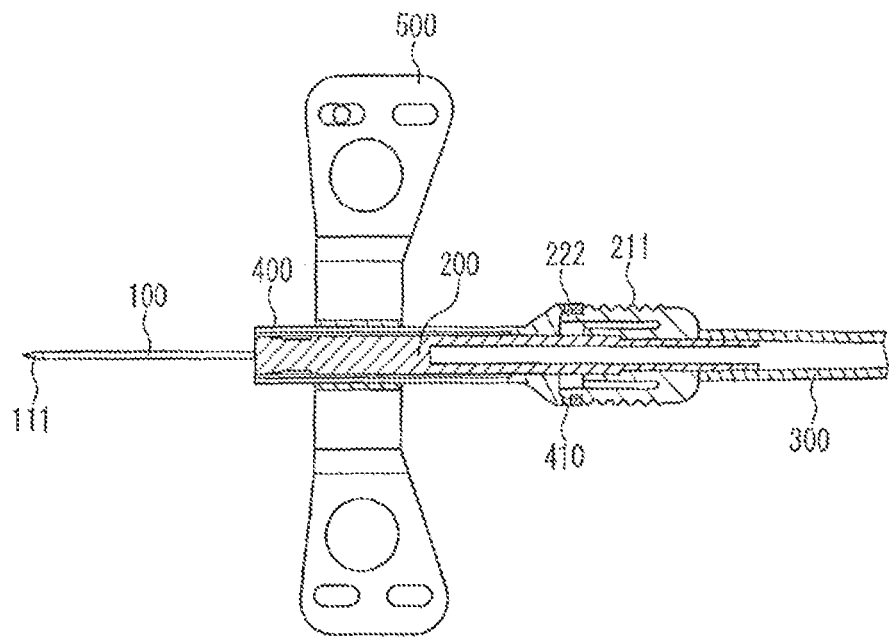
FIG. 19 is a cross-sectional view of another example of the conventional medical needle device.
Figure 20A:
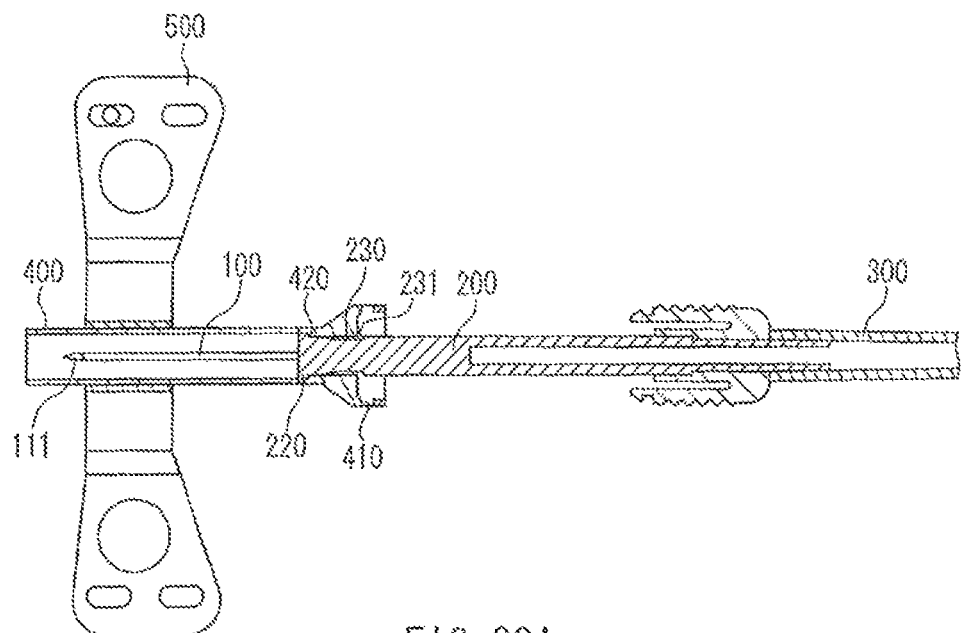
FIG. 20A is a cross-sectional view of the conventional medical needle device shown in FIG. 19, in a state where a rigid needle is stored in a shield tube.
Figure 20B:
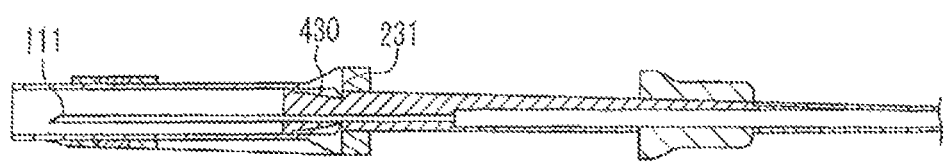
FIG. 20B is another cross-sectional view of the conventional medical needle device shown in FIG. 19, in a state where a rigid needle is stored in a shield tube.

In Embodiment 7, still another example of the medical needle device of the present invention will be explained. FIG. 15 is a cross-sectional view of one example of the medical needle device of the present embodiment, which is cut in an axial direction.

The medical needle device of the present embodiment has a structure that is similar to the medical needle device of Embodiment 1 except that the soft needle 8 and the second hub 7 (see FIG. 2) are not provided and a shape of the first hub 31 is different from that of Embodiment 1.

In Embodiments 1 to 7, the winged medical needle device has been explained above, but the present invention is not limited to this, and can be applied also to a medical needle device having no wing.

The present invention can provide the medical needle device provided with the compact first hub that can be held by the shield reliably during the puncturing operation, and can slide easily inside the shield during the drawing operation.

INDUSTRIAL APPLICABILITY

In the medical needle device of the present invention, the first hub can be held by the shield reliably during the puncturing operation, and the first hub can slide easily inside the shield during the drawing operation. Moreover, since the first hub and the shield can be formed to be compact, the medical needle device of the present invention is preferably used for treatment such as an infusion, a blood transfusion, extracorporeal blood circulation and the like.

The invention claimed is:

1. A medical needle device comprising:
a shield including a substantially cylindrical portion;
a tube;
a first hub that is inserted into an inner bore of the shield movably in an axial direction, whose rear end is connected with the tube;
a rigid needle that is fixed to a front end portion of the first hub; and
a hub movement controlling member that is attached to the shield detachably,
wherein the hub movement controlling member comprises:
a stopper portion that is in the form of a bar and inserted from a rear end side of the shield into the inner bore of the shield exsertably, and has a front end that can be in contact with, but is not fixed to, an end surface of a rear end portion of the first hub in a state that the first hub has reached a movement end on a front end side of the inner bore of the shield, and
a holding portion that can maintain a state where the front end of the stopper portion is in contact with the end surface of the rear end portion of the first hub in the state that the first hub has reached the movement end on the front end side,
the hub movement controlling member is discrete from the shield and the first hub so that the hub movement controlling member can be separated from the first hub by allowing the hub movement controlling member to slide backward away from the shield and the first hub,
the whole of the first hub and a part of the tube connected to the rear end of the first hub are contained within the shield in the state that the first hub has reached the movement end on the front end side, and
when the rigid needle is drawn into the shield and covered with the shield, the hub movement controlling member that has slid backward can be removed from the shield.

2. The medical needle device according to claim 1, further comprising a soft needle that is fixed to a front end portion of the shield and has an inner bore in which the rigid needle can be inserted.

3. The medical needle device according to claim 2,
wherein the shield further comprises a second hub that is fixed to a front end portion of the substantially cylindrical portion, and
the soft needle is fixed to the second hub.

4. The medical needle device according to claim 3, wherein the movement end on the front end side is regulated by the second hub.

5. The medical needle device according to claim 1, wherein the shield further comprises a pair of wing portions that are provided on the front end side of the substantially cylindrical portion.

6. The medical needle device according to claim 5, wherein the pair of wing portions are attached to the substantially cylindrical portion detachably.

7. The medical needle device according to claim 1,
wherein the hub movement controlling member comprises, as the holding portion, a picking portion that is provided extending from a rear end of the stopper portion, has a surface opposing to an outer surface of the shield, and has a convex portion formed on the opposing surface, and
a latching concave portion that corresponds to the convex portion is formed on the outer surface of the shield, and the latching concave portion can be fit with the convex portion while the front end of the stopper portion is in contact with the end surface of the rear end portion of the first hub.

8. The medical needle device according to claim 1,
wherein the hub movement controlling member comprises a lever lock member as the holding portion,
the lever lock member comprises: a pair of pinching portions provided with hook portions that oppose to each other; and a cross-linking portion that cross-links the pair of the pinching portions and connects the pair of the pinching portions with a rear end portion of the stopper portion, and a protruding portion that can be latched with the hook portion is formed on the outer surface of the shield.

9. The medical needle device according to claim 1, wherein the hub movement controlling member comprises, as the holding portion, a pair of cantilever portions that are connected with a rear end portion of the stopper portion, and can decrease a distance therebetween by holding them from both sides for enabling them to hold the substantially cylindrical portion of the shield from the outside thereof.

10. The medical needle device according to claim 9, wherein each of the cantilever portions is disposed around a lateral portion of the substantially cylindrical portion.

11. The medical needle device according to claim 10, wherein the pair of the cantilever portions are arranged axisymmetrically.

12. The medical needle device according to claim 11,
wherein the shield further comprises a pair of wing portions that are provided on the front end side of the substantially cylindrical portion, and
a part of each of the cantilever portions is disposed at the same position as each of the wing portions in an axial direction of the substantially cylindrical portion.

13. The medical needle device according to claim 12, wherein each of the cantilever portions comprises a convex portion for making contact with a wing, which is disposed at a position on the front end side with respect to the wing portion and protrudes toward a lateral direction.

14. The medical needle device according to claim 9, wherein the hub movement controlling member comprises a pair of cantilever portions as the holding portion,
the pair of cantilever portions and the rear end portion of the stopper portion are connected to each other via a substantially semicylindrical portion that covers a part of an upper side circumference of the substantially cylindrical portion of the shield, and a curved part, that are positioned between the pair of cantilever portions and the rear end portion, and
the substantially semicylindrical portion and the pair of cantilever portions are disposed at positions that are slightly away from an outer surface of the substantially cylindrical portion of the shield.

15. The medical needle device according to claim 1,
wherein the first hub has a lateral penetration path that is formed to pierce from a peripheral of the first hub to an inner bore thereof, so that a space formed between an outer surface of the hub and an inner surface of the shield is connected with an inner bore of the hub via the lateral penetration path, and
a sealing portion for keeping a liquid tightness between the outer surface of the hub and the inner surface of the shield is provided on the rear end side of the first hub with respect to the lateral penetration path.

16. The medical needle device according to claim 15, wherein the sealing portion comprises an annular groove and a sealing member that is disposed in the annular groove.

17. The medical needle device according to claim 16,
wherein an annular latching convex portion is provided on the inner surface of the shield,
the first hub comprises: a first large diameter portion and a second large diameter portion that are formed by formation of the annular groove; and a large diameter portion having a bendable piece whose first end is supported by a third large diameter portion, in this order from the front end side, holding by the holding portion in a state where the front end of the stopper portion is in contact with the first hub is released, the first hub moves toward the rear end side of the shield, and the annular latching convex portion is disposed between the second large diameter portion and the large diameter portion having the bendable piece, whereby the rigid needle is drawn into the shield completely, and the first hub is held by the shield so as not to move inside the shield.

18. The medical needle device according to claim 17, wherein the large diameter portion having the bendable piece comprises a plurality of the bendable pieces.

19. The medical needle device according to claim 18, wherein the plurality of the bendable pieces are arranged symmetrically to each other with respect to a center line of the first hub in its longitudinal direction.

20. The medical needle device according to claim 17, wherein the first hub is stored in the shield, in a state where the annular latching convex portion is disposed between the second large diameter portion and the large diameter portion having the bendable piece.

21. The medical needle device according to claim 16,
wherein the first hub comprises: a first large diameter portion and a second large diameter portion that are formed by formation of the annular groove; and a large diameter portion having a bendable piece whose first end is supported by a third large diameter portion, in this order from the front end side,
an inner diameter of the rear end portion of the shield is smaller than an inner diameter of the shield on a front end side with respect to the rear end portion, and the rear end portion has a through hole that is formed to pierce the rear end portion from the outer surface of the substantially cylindrical portion to the inner bore of the substantially cylindrical portion, and
holding by the holding portion in a state where the front end of the stopper portion is in contact with the first hub is released, the first hub moves toward the rear end side of the shield, and a part of the bendable piece is disposed in the through hole, whereby the rigid needle is drawn into the shield completely, and the first hub is retained by the shield so as not to move inside the shield.

22. The medical needle device according to claim 16,
wherein the first hub comprises: a first large diameter portion and a second large diameter portion that are formed by formation of the annular groove; and a third large diameter portion, in this order from the front end side, an annular concave portion is formed between the second large diameter portion and the third large diameter portion,
the substantially cylindrical portion of the shield is provided with a plurality of partition walls, by dividing the rear end portion of the substantially cylindrical portion into plural parts along its circumferential direction, and
a protrusion that can be latched with the annular concave portion is formed on an inner surface of at least one of the partition walls.

23. The medical needle device according to claim 22, wherein an outer diameter of the third large diameter portion becomes smaller gradually from its front end to its rear end.

24. The medical needle device according to claim 16,
wherein an annular latching convex portion is provided on the inner surface of the shield,
the first hub comprises: a first large diameter portion and a second large diameter portion that are formed by formation of the annular groove; and a connecting portion to be connected with the tube, in this order from the front end side, the first hub further comprises a plurality of bendable pieces, each of which has a first end supported by the second large diameter portion and is disposed away from the connecting portion around the connecting portion, and a groove that can be latched with the annular latching convex portion is formed on a surface of each of the bendable pieces opposing to the inner surface of the shield.

25. The medical needle device according to claim 24, wherein the first hub is stored in the shield in a state where the annular latching convex portion is latched with the groove of the bendable piece.

26. The medical needle device according to claim 24, wherein the plurality of the bendable pieces are arranged at an equal interval along a circumferential direction.

27. The medical needle device according to claim 15, further comprising a soft needle that is fixed to a front end portion of the shield and has an inner bore in which the rigid needle can be inserted, wherein the space formed between the outer surface of the first hub and the inner surface of the shield is connected with the inner bore of the soft needle.

28. The medical needle device according to claim 1, wherein the stopper portion and the holding portion are formed integrally.

* * * * *